(12) United States Patent
Williamson et al.

(10) Patent No.: US 6,316,000 B1
(45) Date of Patent: Nov. 13, 2001

(54) CLONING AND EXPRESSION OF PLASMODIUM FALCIPARUM TRANSMISSION-BLOCKING TARGET ANTIGEN, PFS230

(75) Inventors: Kim C. Williamson, Rockville; David C. Kaslow, Kensington, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/954,441

(22) Filed: Oct. 20, 1997

Related U.S. Application Data

(62) Division of application No. 08/323,170, filed on Oct. 13, 1994, now Pat. No. 5,733,772, which is a continuation of application No. 08/010,409, filed on Jan. 29, 1993, now abandoned.

(51) Int. Cl.[7] .................. A61K 39/015; C07K 14/445
(52) U.S. Cl. .................. 424/191.1; 424/268.1; 424/272.1; 530/350; 930/210
(58) Field of Search .............. 530/350; 424/191.1, 424/192.1, 268.1, 272.1; 930/210

(56) References Cited

U.S. PATENT DOCUMENTS 4,707,445 * 11/1987 McCulchan et al. .................. 435/91

OTHER PUBLICATIONS

Kumar et al, Molecular and Biochemical Parasitology 53: 113–120, 1992.*
Williamson et al (Biochemistry 296:359–362, 1992.*
Williamson et al, Molecular and Biochemical Parasitology 75: 33–42, 1995.*
Riley et al, Parasite Immunology 17: 11–19, 1995.*
Murphy et al, Parasitology 100: 177–183, 1990.*
Sandhu et al, Vaccine 12: 56–64, 1994.*
Williamson, K.C., et al., "Immunoaffinity Chromatography Using Electroelution," *Biochemistry*, 296:359–362, 1992.
Williamson, K. et al. (1992) "Cloning and Expression of Plasmodium falciparum transmission blocking target antigen Pfs230", (Abstract of the 41st Annual Meeting of the American Society of Tropical Medicine and Hygiene) *American Journal of Tropical Medicine and Hygiene*, 47(4):94–95.
Triglia, T. et al. (1991) "Large fragments of Plasmodium falciparum DNA can be stable when cloned in yeast artificial chromosomes", *Chemical Abstracts*, 114(11):189.
Lewis, Alan P. (1990) "Cloning and analysis of the gene encoding the 230–kilodalton merozoite surface antigen of Plasmodium yoelii", *Chemical Abstracts*, 112(23):146.
Elliott, J. F., et al., "Novel Gene Encoding A Large *Plasmodium Falciparum* Sexual Stage Specific Antigen Cloned By Expression In Eucaryotic (COS7) Cells", Program and Abstracts of the 40th Annual Meeting of the American Society of Tropical Medicine and Hygiene, Supplement to the American Journal of Tropical Medicine and Hygiene, 45:270, abst.#437 (1991).
Quakyi, I. A., et al., "The 230–kDa Gamete Surface Protein of *Plasmodium falciparum* is also a Target for Transmission–Blocking Antibodies", *Journal of Immunology* 139:4213–4217 (1987).
Barr, P. J., et al., "Recombinant Pfs25 Protein of *Plasmodium falciparum* Elicits Malaria Transmission–Blocking Immunity in Experimental Animals" *Journal of Experimental Medicine* 174:1203–1208 (1991).
Good, M. F., et al., "Limited Immunological Recognition of Critical Malaria Vaccine Candidate Antigens" *Science* 242:574–577 (1988).
Wizel, B. and N. Kumar, "Identification of a Continuous and Cross–Reacting Epitope for *Plasmodium falciparum* Transmission–Blocking Immunity" *Proc. Natl. Acad. Sci.* 88:9533–9537 (1991).
Targett, G., "Immunity to Sexual Stages of Human Malaria Parasites: Immune Modulation During Natural Infections, Antigenic Determinants, and the Induction of Transmission-Blocking Immunity" *Scand. J. Infect. Dis. Suppl.* 76:79–88 (1990).
Ong, C. S. L., et al., "The Primary Antibody Response of Malaria Patients to *Plasmodium falciparum* Sexual Stage Antigens which are Potential Transmission Blocking Vaccine Candidates" *Parasite Immunology* 12:447–456 (1990).
Foo, A., et al., "Conserved and Variant Epitopes of Target Antigens of Transmission–Blocking Antibodies Among Isolates of *Plasmodium falciparum* from Malaysia" *Am. J. Trop. Med. Hyg.* 44:623–631 (1991).
Sambrook, Molecular Cloning, A Laboratoty Manual, 2nd Ed Spring Harbor Laboratory, CS11, NY (1989).*
Dane et al Science vol. 225 pp. 593–599 (1984).*

* cited by examiner

Primary Examiner—Mary E. Mosher
(74) Attorney, Agent, or Firm—Townsend and Townsend and Crew LLC

(57) ABSTRACT

Compositions comprising biologically pure Pfs230 and nucleic acids which encode them are provided. The proteins can be used induce transmission blocking immune responses in susceptible hosts.

11 Claims, 6 Drawing Sheets

CLONING AND EXPRESSION OF PLASMODIUM FALCIPARUM TRANSMISSION-BLOCKING TARGET ANTIGEN, PFS230

This is a Division of application Ser. No. 08/323,170 filed Oct. 13, 1994, now U.S. Pat. No. 5,733,772 which is a FWC of Ser. No. 08/010,409 filed Jan. 29, 1993, abandoned.

BACKGROUND OF THE INVENTION

Malaria continues to exact a heavy toll on humans. Between 200 million to 400 million people are infected by *Plasmodium falciparum*, the deadliest of the malarial protozoans, each year. One to four million of these people die. Approximately 25 percent of all deaths of children in rural Africa between the ages of one and four years are caused by malaria.

The life cycle of the malaria parasite is complex. Infection in man begins when young malarial parasites or sporozoites are injected into the bloodstream of a human by a mosquito. After injection the parasite localizes in liver cells. Approximately one week after injection, the parasites or merozoites are released into the bloodstream to begin the erythrocytic phase. Each parasite enters a red blood cell in order to grow and develop. When the merozoite matures in the red blood cell, it is known as a trophozoite and, when fully developed, as a schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or macrogametocyte and the male parasite or microgametocyte. These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete and a macrogamete. The fertilized parasite, which is known as a zygote, then develops into an ookinete. The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Malaria vaccines are needed against different stages in the parasite's life cycle, including the sporozoite, asexual erythrocyte, and sexual stages. Each vaccine against a particular life cycle stage increases the opportunity to control malaria in the many diverse settings in which the disease occurs. For example, sporozoite vaccines fight infection immediately after injection of the parasite into the host by the mosquito. First generation vaccines of this type have been tested in humans. Asexual erythrocytic stage vaccines are useful in reducing the severity of the disease. Multiple candidate antigens for this stage have been cloned and tested in animals and in humans.

However, as drug-resistant parasite strains render chemoprophylaxis increasingly ineffective, a great need exists for a transmission-blocking vaccine. Such a vaccine would block the portion of the parasite's life cycle that takes place in the mosquito or other arthropod vector, thus preventing even the initial infection of humans. Several surface antigens serially appear on the parasite as it develops from gametocyte to gamete to zygote to ookinete within the arthropod midgut (Rener et al., *J. Exp. Med.* 158: 976–981, 1983; Vermeulen et al., *J. Exp. Med.* 162: 1460–1476, 1985). Although some of these antigens induce transmission-blocking antibodies, their use in developing transmission blocking vaccines may be limited. For instance, the antigens may fail to generate an immune response in a broad segment of the vaccinated population. Others may only produce partial blocking of transmission.

Thus there is a need to develop transmission-blocking vaccines which induce high, long lasting antibody titers and which can be produced in large amounts at low cost. The present invention addresses these and other needs.

SUMMARY OF THE INVENTION

The present invention provides biologically pure Pfs230 polypeptides which preferably have an epitope capable of eliciting a transmission blocking immune response. The sequence of the full length protein is set forth in SEQ. ID. No. 2. The invention also provides recombinantly produced Pfs230 and isolated nucleic acids which encodes the polypeptides. The sequence of a nucleic acid which encodes the full length protein is set forth in SEQ. ID. No. 1.

Also disclosed are expression vectors comprising a promoter operably linked to a nucleic acid which encodes Pfs230 as well as cells comprising the vectors. In one embodiment, the expression vector is capable of directing expression in *E. coli*.

The invention further provides pharmaceutical compositions comprising a pharmaceutically acceptable carrier and Pfs230 in an amount sufficient to induce a transmission blocking immune response in a susceptible organism, such as a human. The Pfs230 is preferably an immunologically active fragment of the full length protein. Methods of preventing transmission of malaria comprising administering to a susceptible organism the pharmaceutical compositions are also disclosed.

DEFINITIONS

The term "Pfs230" refers to proteins expressed on the surface of *Plasmodium falciparum* gametocytes which have a molecular weight of about 360 kDa before processing. The term encompasses native proteins as well as recombinantly produced proteins that induce a transmission blocking immune response. It also includes immunologically active fragments of these proteins. "Immunologically active fragments" are those portions of the full length protein which comprise epitopes capable of eliciting a transmission blocking immune response or which are recognized by transmission blocking antibodies.

A "susceptible organism" is a Plasmodium host that is susceptible to malaria, for example, humans and chickens. The particular susceptible organism or host will depend upon the Plasmodium species.

The phrases "biologically pure" or "isolated" refer to material which is substantially or essentially free from components which normally accompany it as found in its native state. Typically, a protein is substantially pure when at least about 95% of the protein in a sample has the same amino acid sequence. Usually, protein that has been isolated to a homogenous or dominant band on a polyacrylamide gel, trace contaminants in the range of 5–10% of native protein which co-purify with the desired protein. Biologically pure material does not contain such endogenous co-purified protein.

Two sequences (either nucleic acids or polypeptides) are said to be "substantially identical" if greater than about 85% of the sequences are shared when optimally aligned and compared. Greater identity of more than about 90% is preferred, and about 95% to absolute identity is most preferred.

Another indication that nucleic sequences are substantially identical is if they hybridize to the same complementary sequence under stringent conditions. Stringent conditions will depend upon various parameters (e.g. GC content) and will be different in different circumstances. Generally, stringent conditions for nucleic acids isolated from *Plasmodium falciparum* are those in which the salt concentration is at least about 0.2 molar and the temperature is at least about 55° C.

BRIEF DESCRIPTION OF THE FIGURES

FIG. 6A is indirect immunofluorescence of intact gametes/zygotes using rPfs230/MBP-A antisera. FIG. 6B is the corresponding bright field image.

FIG. 7A is indirect immunofluorescence of intact gametes/zygotes using rPfs230/MBP-B antisera. FIG. 7B is the corresponding bright field image.

FIG. 8A is indirect immunofluorescence of intact gametes/zygotes using MBP antisera. FIG. 8B is the corresponding bright field image.

DESCRIPTION OF THE PREFERRED EMBODIMENT

Figure 1:
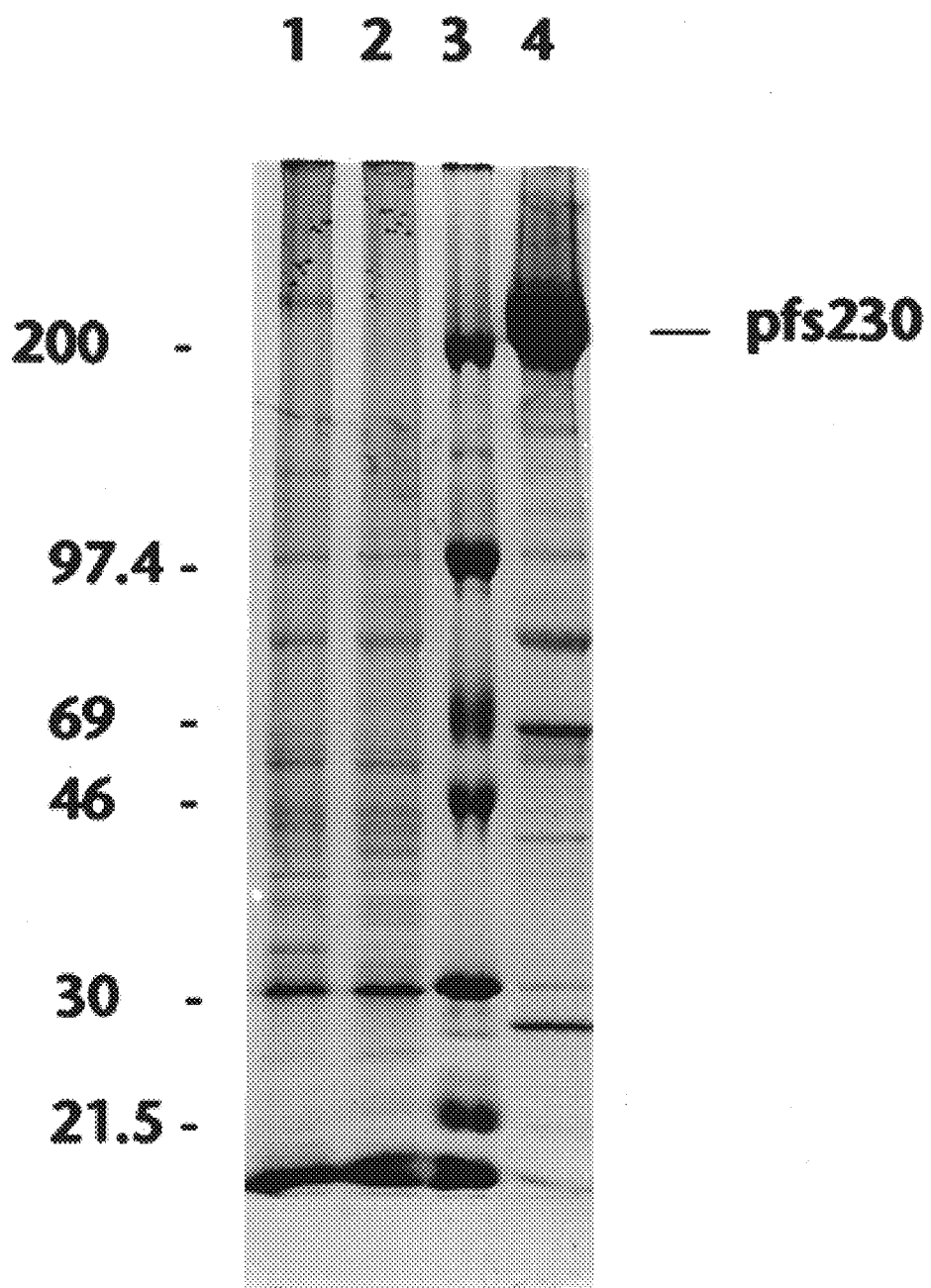
FIG. 1 shows the results of the samples from each of the purification steps which were size-fractionated on a 4–20% SDS-polyacrylamide gel and stained with coomassie blue. The lanes in the gel are as follows: Gamete\zygote extract before 1B3-Sepharose resin (lane 1), proteins that did not bind to the 1B3-Sepharose resin (lane 2), molecular weight standards (Amersham) (lane 3) and protein electroeluted from 1B3-Sepharose resin (lane 4). The molecular weight (Mr×10−3) is indicated on the left and the position of Pfs230 is indicated on the right.

The present invention provides recombinantly produced Pfs230 and fragments derived from the protein that are useful for inducing an immune response when injected into a human or other host animal. Pfs230 and homologs in other Plasmodium species can be used to block transmission of a number of parasites associated with malaria. Four species of the genus Plasmodium infect humans, *P. vivax, P. ovale, P. malariae*, and *P. falciparum*. In addition other Plasmodium species infect other animals. For instance, *P. gallinaceum* is responsible for avian malaria.

Pfs230 Protein

Pfs230 is expressed by the parasite while it undergoes gametocytogenesis in the human host. This antigen has been identified on day 2 of gametocytogenesis and continues to be produced as the gametocyte is taken up by the mosquito in a blood meal and emerges from the erythrocyte in the mosquito midgut. Once the parasite emerges from the erythrocyte, Pfs230 is exposed on the surface of the parasite, and is thus in contact with the components of the bloodmeal including antibodies and complement.

The 9.4 kb open reading frame of the nucleic acid encoding Pfs230 predicts a protein with a molecular weight of 363,243 Daltons. Pfs230 exists in at least two forms, a 360 kDa form that does not radiolabel with $^{125}$I and a $^{125}$I radiolabeled form isolated from surface labeled gametes. The labeled form when sized under reducing conditions migrates as a 310,000 molecular weight band. These results suggest that the full-length 360 kDa protein is processed to a 310 kDa protein that is expressed on the surface of the gamete.

A prior art MAb 1B3 has been reported to immunoprecipitate a 230 kDa protein from radiolabeled surface proteins of newly formed gametes and zygotes. This monoclonal antibody was reported to recognize two proteins of 260,000 and 230,000 Mr on western blots. Quakyi, et al., *J. Immunol.* 139:4213–4217 (1987), which is incorporated herein by reference. Evidence provided here shows that the protein encoded by the gene of the present invention is the same protein as that recognized by MAb 1B3. In particular, antisera raised against fusion proteins expressed from the nucleic acids of the invention recognized bands similar to those reported for Pfs230. The antisera also immunoprecipitates $^{125}$I-labeled Pfs230 and reacts with the surface of intact gametes as assayed by indirect immunofluorescence.

SEQ. ID. No. 2 is the deduced amino acid sequence of the 9.4 kB gene. The deduced amino acid sequence of Pfs230 codes for a 363 kDa polypeptide having five distinct characteristics: 1) consistent with Pfs230 being a non-integral membrane protein (Kumar & Wizel, *Mol. Biochem. Parasitol.*, 53: 113–120 (1992)), there is a presumptive signal sequence at the amino-terminus, but no other predicted hydrophobic or transmembrane regions; 2) starting at amino acid 280, there are 25 contiguous E residues; 3) beginning with amino acid 379, a four amino acid (E-E-V-G) (SEQ. ID. NO. 3) repeat is repeated tandemly 8 times followed by 4 copies of an eight amino acid (E-E-V-G-E-E/G-E/V-G) (SEQ. ID. No. 4) repeat; 4) there are three regions of highly negative net charge, including amino acids 273–325, which contain the 25 E residues, amino acids 1147–1205, and amino acids 1604–1668; and 5) there are six copies of a seven cysteine motif with the consensus sequence.

The Pfs230 proteins of the invention may be recombinantly produced or may be purified from parasites isolated from infected host organisms. Methods for purifying desired proteins are well known in the art and are not presented in detail here. For a review of standard techniques see, Methods in Enzymology, "Guide to Protein Purification", M. Deutscher, ed. Vol. 182 (1990), which is incorporated herein by reference. For instance, Pfs230 or its homologs in other species can be purified using affinity chromatography, SDS-PAGE, and the like.

Nucleic Acids

Another aspect of the present invention relates to the cloning and recombinant expression of Pfs230 and its homologs. The recombinantly expressed polypeptides can be used in a number of ways. For instance, they can be used as transmission-blocking vaccines, as described below. The recombinantly produced proteins can also be used for raising antibodies or for T cell and B cell epitope mapping. In addition, oligonucleotides from the cloned genes can be used as probes to identify homologous polypeptides in other species. The invention relies on routine techniques in the field of recombinant genetics, well known to those of ordinary skill in the art. A basic text disclosing the general methods of use in this invention is Sambrook et al., *Molecular Cloning, A Laboratory Manual*, Cold Spring Harbor Publish., Cold Spring Harbor, N.Y. 2nd ed. (1989), which is incorporated herein by reference.

Pfs230 was immunoaffinity purified using mAb 1B3 as described in detail below. The isolated protein was then digested with trypsin. The tryptic peptides were separated by reverse phase HPLC and three well resolved peptides were microsequenced. From this amino acid sequence degenerate oligonucleotide probes were used to screen a *P. falciparum* sexual stage cDNA library.

Other methods for isolating genes encoding Pfs230 and its homologs can also be used. For instance, the amino acid sequence of the N-terminus can be determined and degenerate oligonucleotide probes, designed to hybridize to the desired gene, are synthesized. Amino acid sequencing is performed and oligonucleotide probes are synthesized according to standard techniques as described, for instance, in Sambrook et al., supra.

Oligonucleotide probes useful for identification of desired genes can also be prepared from conserved regions of related genes in other species. For instance, probes derived from a gene encoding Pfs230 may be used to screen libraries for homologous genes from other parasites of interest.

Other methods include the detection of restriction fragment length polymorphisms (RFLP) between wild type and mutant strains lacking a Pfs230 polypeptide. Amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

Genomic or cDNA libraries are prepared according to standard techniques as described, for instance, in Sambrook, supra. To construct genomic libraries, large segments of genomic DNA are generated by random fragmentation or restriction enzyme degradation and are ligated with vector DNA to form concatemers that can be packaged into the appropriate vector. Two kinds of vectors are commonly used for this purpose, bacteriophage lambda vectors and plasmids.

To prepare cDNA, mRNA from the parasite of interest is first isolated. Eukaryotic MRNA has at its 3' end a string of adenine nucleotide residues known as the poly-A tail. Short chains of oligo d-T nucleotides are then hybridized with the poly-A tails and serve as a primer for the enzyme, reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or phage vector for propagation in *E. coli*.

Identification of clones in either genomic or CDNA libraries harboring the desired nucleic acid segments is performed by either nucleic acid hybridization or immunological detection of the encoded protein, if an expression vector is used. The bacterial colonies are then replica plated on solid support, such as nitrocellulose filters. The cells are lysed and probed with either oligonucleotide probes described above or with antibodies to the desired protein.

Standard transfection methods are used to produce prokaryotic, mammalian, yeast or insect cell lines which express large quantities of the Pfs230 polypeptide, which is then purified using standard techniques. See, e.g., Colley et al., *J. Biol. Chem.* 264:17619–17622, 1989; and Guide to Protein Purification, supra.

The nucleotide sequences used to transfect the host cells can be modified to yield the Pfs230 polypeptide or fragments thereof, with a variety of desired properties. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring Pfs230.

For instance, immunogenically active fragments comprising about 6 to about 300 amino acids are typically used. Shorter fragments comprising bout 100 to about 200 amino acids, preferably about 130 to about 160, may also be used. For use as vaccines, immunologically active fragments are typically preferred so long as at least one epitope capable of eliciting transmission blocking antibodies remains. Preferred polypeptide fragments of the invention include those comprising one or more of the six copies of the seven-cysteine motif noted above. Other modifications include the addition of a membrane anchoring sequence to the expressed protein. Such modifications allow the protein to be expressed on cell surfaces and thereby improve immunogenicity.

In general, modifications of the sequences encoding the homologous polypeptides may be readily accomplished by a variety of well-known techniques, such as site-directed mutagenesis (see, Gillman and Smith, Gene 8:81–97, 1979) and Roberts, S. et al., *Nature* 328:731–734, 1987). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit transmission blocking can be easily determined using the mosquito feeding assays, described in Quakyi et al., supra. In addition, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

The particular procedure used to introduce the genetic material into the host cell for expression of the Pfs230 polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses. SV40 vectors include pSVT7 and pMT2. Vectors derived from bovine papilloma virus include pBV-1MTHA, and vectors derived from Epstein Bar virus include pHEBO, and p205. Other exemplary vectors include pRE4, pMSG, pAV009/$A^+$, pMTO10/$A^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, cytomegalovirus promoter, or other promoters shown effective for expression in eukaryotic cells.

The expression vector typically contains a transcription unit or expression cassette that contains all the elements required for the expression of the Pfs230 polypeptide DNA in the host cells. A typical expression cassette contains a promoter operably linked to the DNA sequence encoding a Pfs230 polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

The DNA sequence encoding the Pfs230 polypeptide will typically be linked to a cleavable signal peptide sequence to promote secretion of the encoded protein by the transformed cell. Additional elements of the cassette may include selectable markers, enhancers and, if genomic DNA is used as the structural gene, introns with functional splice donor and acceptor sites.

Enhancer elements can stimulate transcription up to 1,000 fold from linked homologous or heterologous promoters. Enhancers are active when placed downstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Pres, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

Efficient expression and secretion in yeast is conveniently obtained using expression vectors based on those disclosed in Barr et al., *J. Biol. Chem.* 263: 16471–16478, 1988, or U.S. Pat. No. 4,546,082, which are incorporated herein by reference. In these vectors the desired sequences are linked to sequences encoding the yeast α-factor pheromone secretory signal/leader sequence. Suitable promoters to use include the ADH2/GAPDH hybrid promoter as described in Cousens et al., *Gene* 61:265–275 (1987), which is incorporated herein by reference. Yeast cell lines suitable for the present invention include BJ 2168 (Berkeley Yeast Stock Center) as well as other commonly available lines.

Any of a number of other well known cells and cell lines can be used to express the polypeptides of the invention. For instance, prokaryotic cells such as *E. coli* can be used. Eukaryotic cells include, Chinese hamster ovary (CHO) cells, COS cells, mouse L cells, mouse A9 cells, baby hamster kidney cells, C127 cells, PC8 cells, and insect cells.

Following the growth of the recombinant cells and expression of the Pfs230 polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the Pfs230 polypeptide can be accomplished by standard techniques, for example, affinity chromatography, ion exchange chromatography, sizing chromatography, $His_6$ tagging and Ni-agarose chromatography (as described in Dobeli et al. *Mol. and Biochem. Parasit.* 41:259–268 (1990)), or other protein purification techniques to obtain homogeneity. The purified proteins are then used to produce pharmaceutical compositions, as described below.

Transmission-blocking Antibodies

A further aspect of the invention includes antibodies against Pfs230 or its homologous polypeptides. The antibodies are useful for blocking transmission of parasites. Thus, antibodies can be used as therapeutic agents to block transmission.

The multitude of techniques available to those skilled in the art for production and manipulation of various immunoglobulin molecules can be readily applied to block transmission. As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. Immunoglobulins may exist in a variety of forms besides antibodies, including for example, Fv, Fab, and $F(ab)_2$, as well as in single chains. For a general review of immunoglobulin structure and function see, *Fundamental Immunology*, 2d Ed., W. E. Paul ed., Ravens Press, N.Y., (1989) which is incorporated herein by reference.

Monoclonal antibodies which bind Pfs230 can be produced by a variety of means. The production of non-human monoclonal antibodies, e.g., murine, lagomorpha, equine, etc., is well known and may be accomplished by, for example, immunizing the animal with a preparation containing Pfs230. Antibody-producing cells obtained from the immunized animals are immortalized and screened, or screened first for the production antibodies which bind Pfs230 and then immortalized. For a discussion of general procedures of monoclonal antibody production see Harlow and Lane, *Antibodies, A Laboratory Manual* Cold Spring Harbor Publications, N.Y. (1988), which is incorporated herein by reference.

It may be desirable to transfer the antigen binding regions of the non-human antibodies, e.g., the $F(ab')_2$ or hypervariable regions, to human constant regions (Fc) or framework regions by recombinant DNA techniques to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences which encode a human monoclonal antibody or portions thereof that specifically bind to Pfs230 by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

Vaccines

The Pfs230 polypeptides of the present invention are also useful as prophylactics, or vaccines, for blocking transmission of malaria or other diseases caused by parasites. Compositions containing the polypeptides are administered to a subject, giving rise to an anti-Pfs230 polypeptide immune response. The Pfs230 polypeptide-specific antibodies then block transmission of the parasite from the subject to the arthropod vector, preventing the parasite from completing its life cycle. An amount of prophylactic composition sufficient to result in blocking of transmission is defined to be an "immunologically effective dose."

The isolated nucleic acid sequence coding for Pfs230 or its homologous polypeptides can also be used to transform viruses which transfect host cells in the susceptible organism. Live attenuated viruses, such as vaccinia or adenovirus, are convenient alternatives for vaccines because they are inexpensive to produce and are easily transported and administered. Vaccinia vectors and methods useful in immunization protocols are described in, e.g., U.S. Pat. No. 4,722,848, incorporated herein by reference.

Suitable viruses for use in the present invention include, but are not limited to, pox viruses, such as, canarypox and cowpox viruses, and vaccinia viruses, alpha viruses, adenoviruses, and other animal viruses. The recombinant viruses can be produced by methods well known in the art: for example, using homologous recombination or ligating two plasmids together. A recombinant canarypox or cowpox virus can be made, for example, by inserting the gene encoding the Pfs230, immunologically active segment of Pfs230 or other homologous polypeptide into a plasmid so that it is flanked with viral sequences on both sides. The gene is then inserted into the virus genome through homologous recombination.

The recombinant virus of the present invention can be used to induce anti-Pfs230 polypeptide antibodies in mammals, such as mice or humans. In addition, the recombinant virus can be used to produce the Pfs230 polypeptides by infecting host cells which in turn express the polypeptide.

The present invention also relates to host cells infected with the recombinant virus of the present invention. The host cells of the present invention are preferably eukaryotic, such as yeast cells, or mammalian, such as BSC-1 cells. Host cells infected with the recombinant virus express the Pfs230 polypeptides on their cell surfaces. In addition, membrane extracts of the infected cells induce transmission blocking antibodies when used to inoculate or boost previously inoculated mammals.

In the case of vaccinia virus (for example, strain WR), the sequence encoding the Pfs230 polypeptides can be inserted into the viral genome by a number of methods including homologous recombination using a transfer vector, pTKgpt-OFIS as described in Kaslow et al., *Science* 252:1310–1313, 1991, which is incorporated herein by reference.

The Pfs230 polypeptides, or recombinant viruses of the present invention can be used in pharmaceutical and vaccine compositions that are useful for administration to mammals, particularly humans, to block transmission of a variety of infectious diseases. The compositions are suitable for single administrations or a series of administrations. When given as a series, inoculations subsequent to the initial administration are given to boost the immune response and are typically referred to as booster inoculations. Suitable formulations are found in *Remington's Pharmaceutical Sciences*, Mack Publishing Company, Philadelphia, Pa. 17th ed. (1985), which is incorporated herein by reference.

The pharmaceutical compositions of the invention are intended for parenteral or oral administration. Preferably, the pharmaceutical compositions are administered parenterally, e.g., subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

In therapeutic applications, Pfs230 polypeptides or viruses of the invention are administered to a patient in an amount sufficient to prevent parasite development in the arthropod and thus block transmission of the disease. An amount adequate to accomplish this is defined as a "therapeutically effective dose." Amounts effective for this use will depend on, e.g., the particular polypeptide or virus, the manner of administration, the weight and general state of health of the patient, and the judgment of the prescribing physician.

The vaccines of the invention contain as an active ingredient an immunogenically effective amount of the Pfs230 polypeptides or recombinant virus as described herein. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. In addition, the compositions can be administered in slow release particles as described in Langer, *Science* 249:1527–1533 (1990).

Vaccine compositions containing the polypeptides or viruses of the invention are administered to a patient to elicit a transmission-blocking immune response against the antigen and thus prevent spread of the disease through the arthropod vector. Such an amount is defined as an "immunogenically effective dose." In this use, the precise amounts again depend on the patient's state of health and weight, the mode of administration, and the nature of the formulation, but generally range for the initial immunization (that is for therapeutic or prophylactic administration) from about 1.0 μg to about 1 mg of peptide for a 70 kg patient, followed by boosting dosages of from about 1.0 μg to about 100 μg of peptide pursuant to a boosting regimen over weeks to months.

The following examples are offered by way of illustration, not by way of limitation.

EXAMPLE 1

Isolation of Pfs230

Pfs230 was immunoaffinity purified using monoclonal 1B3 (mAb 1B3) (Quakyi, et al., *J. Immunol.*, 139: 4213–4217 (1987)). It was electroeluted from mAb 1B3-resin prepared as described in Williamson, et al., *Anal. Biochem.*, 206: 359–362 (1992), reduced and alkylated, run in one lane of a 4% gel and then transferred electrophoretically to nitrocellulose. The band corresponding to Pfs230 was excised then digested in situ with trypsin. The tryptic peptides were separated by reverse phase HPLC and three well resolved peptides were microsequenced. From this amino acid sequence degenerate oligonucleotide probes were designed utilizing *P. falciparum* codon bias and used to screen a *P. falciparum* sexual stage cDNA library prepared according to standard techniques.

FIG. 1 shows the results of the samples from each of the purification steps which were size-fractionated on a 4–20% SDS-polyacrylamide gel and stained with coomassie blue. The lanes in gel are as follows: Gamete/zygote extract before 1B3-Sepharose resin (lane 1), proteins that did not bind to the 1B3-Sepharose resin (lane 2), molecular weight standards (Amersham) (lane 3) and protein electroeluted from 1B3-Sepharose resin (lane 4). The molecular weight (Mr×10$^3$) is indicated on the left and the position of Pfs230 is indicated on the right.

Oligonucleotide probes from each of the three tryptic peptides hybridized to a 4.4 kB insert of an isolated clone. Sequencing revealed open reading frames at both the 5' and 3' ends of the 4.4 kB clone, therefore synthetic oligonucleotides probes corresponding to the ends were used to rescreen the library and obtain overlapping clones that extend the sequence. This process was continued until cDNA clones covering the entire 9.4 kB open reading frame were isolated. The deduced amino acid sequence of the 9.4 kB gene (SEQ. ID. No. 2) contains all 3 tryptic peptides that were microsequenced.

Figure 2:
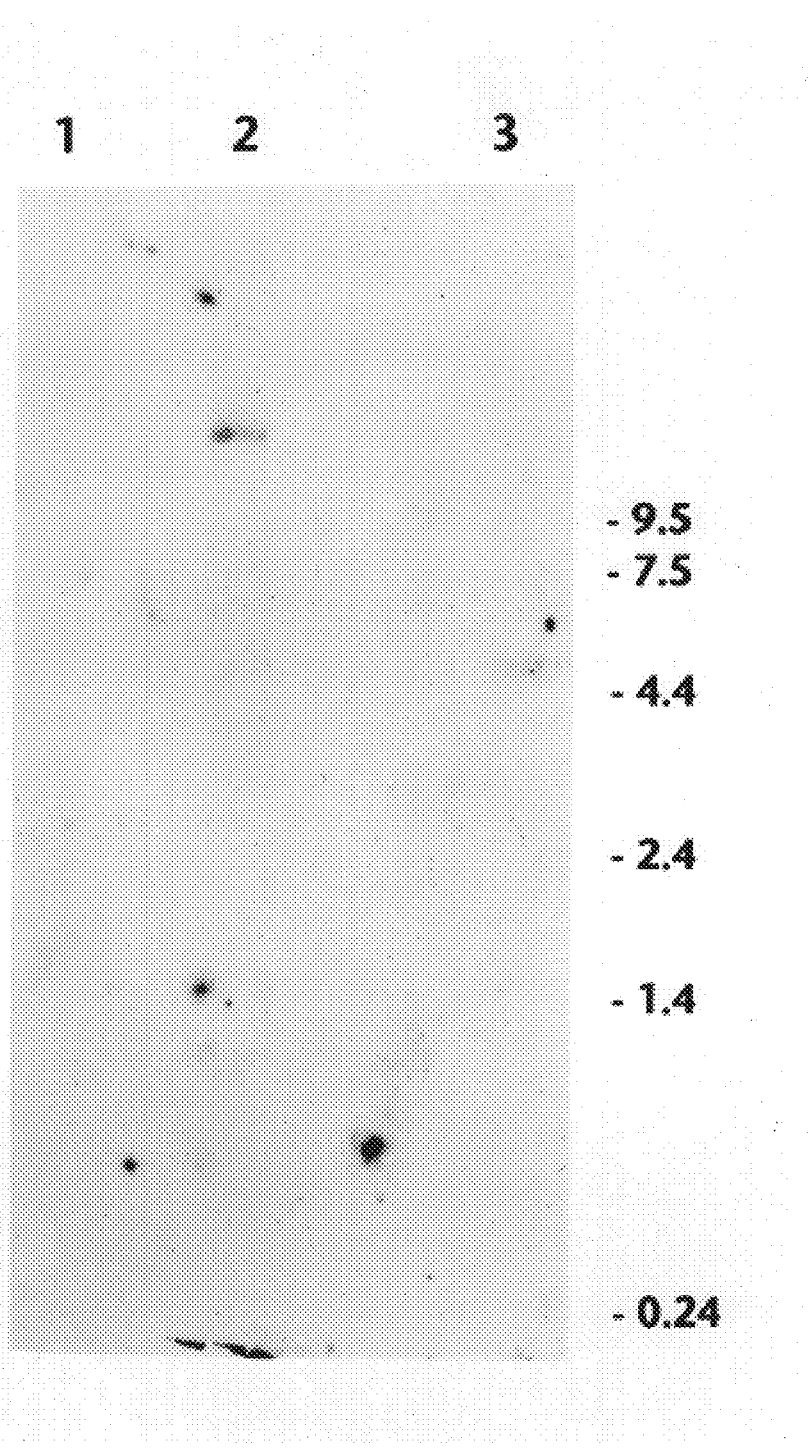
FIG. 2 shows Northern analysis of *P. falciparum* RNA from various stages in the life cycle. Lane 1 comprises RNA from an asexual stage, lane 2 is RNA from gametocytes (stage 2 & 3), and lane 3 is RNA from zygotes/gametes (5 hours post emergence). The blot was probed with the random-primer labeled 4.4 kb insert.

The Pfs230 RNA transcript is 12.5 kB and sexual stage-specific as shown in the Northern analysis of *P. falciparum* RNA in FIG. 2. Equal amounts of RNA were run in each lane (1) asexual, (2) gametocytes (stage 2 & 3), and (3) zygotes/gametes (5 hours post emergence). The blot was probed with the random-prime labeled 4.4 kb insert described above. The message is most abundant in gametocytes. With a long exposure of the northern a faint band can be seen in RNA from 5 hour zygotes but there is no band with asexual RNA. Oligonucleotide probes from the extreme 5' and 3' ends of the ORF hybridize to what appears to be the same transcript.

The 9.4 kB open reading frame predicts a protein with a molecular weight of 363,243 kDa, this is larger than the 260,000 and 230,000 Mr reported for the proteins mAb 1B3 recognizes by western blot. Only the 230,000 band was shown to be radiolabeled when live gametes were surface-labeled with $^{125}$I. Since mAb 1B3 does not react with reduced Pfs230 it has been difficult to obtain an accurate molecular weight of the protein. Quakyi, et al., supra.

Figure 3:
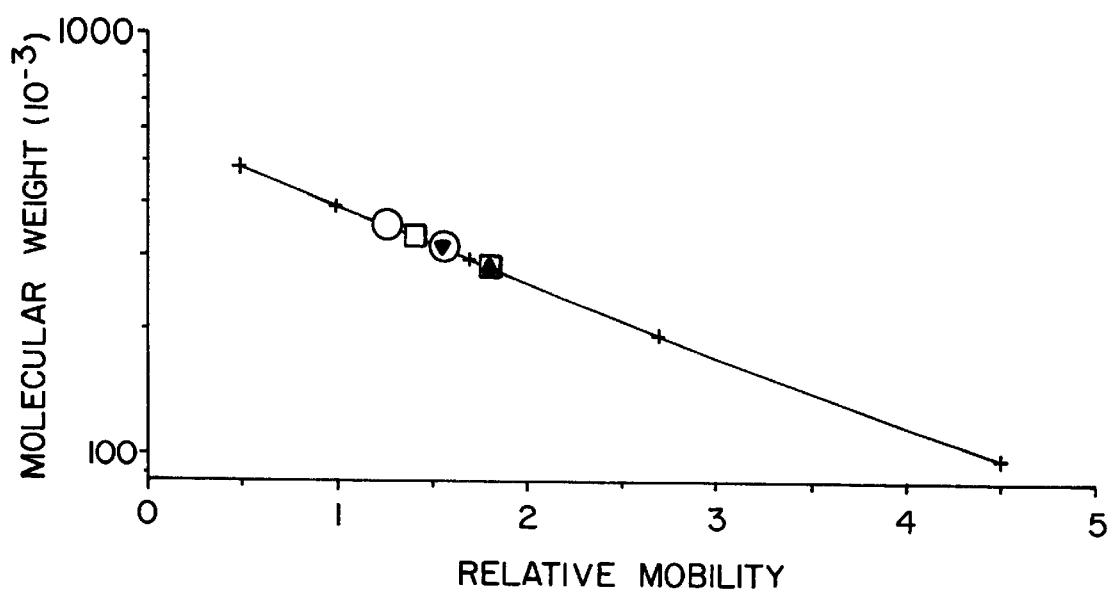
FIG. 3 shows molecular weight determination of Pfs230. Proteins from $^{125}$I-surface-labeled gametes were size-fractionated on a 4% polyacrylamide gel under nonreducing (□, ▲) and reducing (○, ▼) conditions, then transferred to nitrocellulose and immunoblotted with a 1:500 dilution of rPfs230/MBP-A antisera. The relative mobility of molecular weight markets (+), $^{125}$I-labeled Pfs230 (▲, ▼) and rPfs230/MBP-A immunoreactive bands (□, ○) was plotted.

Prior art estimates of the size of the protein have been made with molecular weight standards having molecular weights less than 200 kDa. To more accurately determine the molecular weight, radiolabeled Pfs230 from surface labeled gametes was carefully sized under reducing conditions using molecular weight markers ranging from 100,000 to 500,000. Reduced $^{125}$I labeled Pfs230 migrated as a 310,000 molecular weight band (FIG. 3).

Figure 4A:
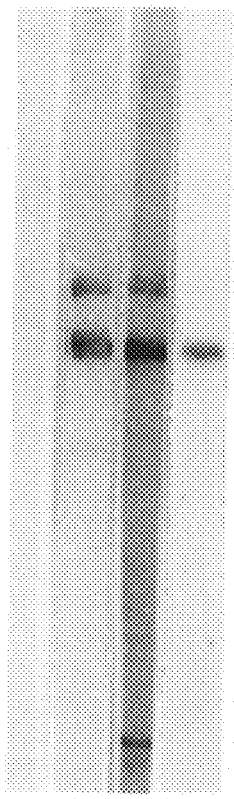
FIGS. 4A and 4B show Western blots of Triton X-100 extracted $^{125}$I-surface-labeled gametes/zygotes size-fractionated on a 4% polyacrylamide gel under (A) nonreducing or (B) reducing conditions and reacted with a 1:5,000 dilution of MBP antisera (lane 1), rPfs230/MBP-A antisera (lane 2), and rPfs230/MBP-B antisera (lane 3). Also shown is an autoradiograph of the rPfs230/MBP-B lane (lane 4). The M$_r$ standards (×10$^{-3}$) are indicated.
Figure 4B:
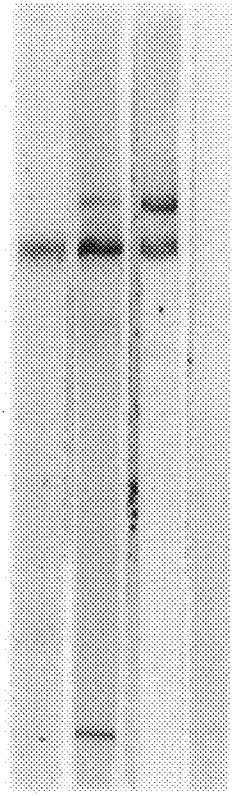

To confirm that the cloned gene was indeed Pfs230, antibodies to a 2.0–2.2 kB section of the gene expressed in *E. coli* as fusions with maltose-binding protein (rPfs230/MBP-A E-B, described below) were used to assay a western blot of Triton X-100 extracted *P. falciparum* gametes/zygotes. FIGS. 4A and 4B show Western blots of Triton X-100 extracted $^{125}$I-surface-labeled gametes reacted with a 1:5,000 dilution of MPB antisera (lane 1), rPfs230/MBP-A antisera (lane 2), and rPfs230/MBP-B antisera (lane 3). Also shown is an autoradiograph of rPfs230/MBP-B (lane 4).

When the extract was size-fractionated under nonreducing conditions the rPfs230/MBP-A and -B antisera recognized bands of 325,000 kDa and 275,000 kDa, and under reducing conditions bands of 360,000 kDa and 310,000 kDa (FIGS. 4A and 4B, respectively). Neither preimmune sera nor antisera to MBP alone reacted with any specific bands.

The lower bands, under both reducing and nonreducing conditions comigrated with $^{125}$I labeled Pfs230 (FIGS. 4A and 4B). This suggests that only the lower band was exposed on the surface of the gamete. Possibly, the 360,000 protein is processed to a 310,000 form as it is moved to the surface of the gamete.

Figure 5:
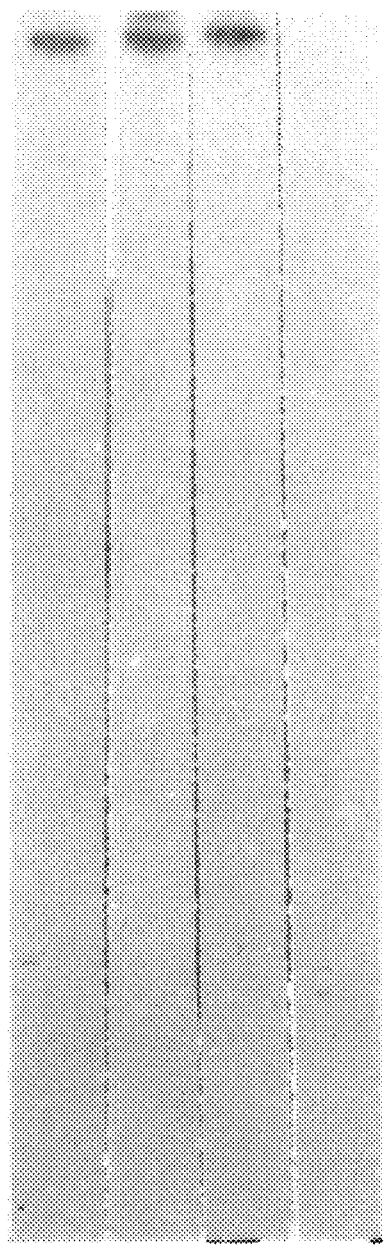
FIG. 5 shows immunoprecipitation of radiolabeled Pfs230 from a Triton X-100 extract of $^{125}$I-surface-labeled gametes/zygotes. mAb 1B3 (lane 1), rPfs230/MBP-A antisera (lane 2), rPfs230/MBP-B antisera (lane 3) and MBP antisera (lane 4) were incubated with extract, then precipitated with protein A-sepharose. The precipitated material was size-fractionated on a 4–20% polyacrylamide gel and the radiolabeled bands were visualized by autoradiography.

To determine whether the rPfs230/MBP antisera recognized the native (nondenatured) surface form of Pfs230, the antisera was used to immunoprecipitate radiolabeled Pfs230 from a Triton X-100 extract of surface-labeled *P. falciparum* gametes/zygotes (FIG. 5). Proteins immunoprecipitated by the following antibodies or antisera were loaded on the gel: mAb 1B3 (lane 1), rPfs230/MBP A antisera (lane 2), rPfs230/MBP-B (lane 3) and MBP antisera (lane 4). The antibodies and antisera were incubated with a Triton X-100 extract of $^{125}$-I surface labeled gametes and precipitated with protein A-sepharose as described above. The precipitated material was run out on a 4–20% acrylamide gel. The radiolabeled bands were visualized by autoradiography. FIG. 5 shows that $^{125}$I-labeled Pfs230 was precipitated by rPfs230/MBP 1B antisera and monoclonal 1B3 but not MBP antisera.

Figure 6:
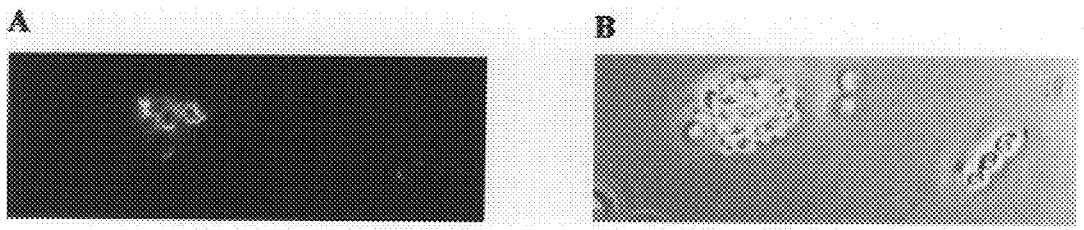
FIGS. 6A and 6B show indirect immunofluorescence assay of intact gametes/zygotes.
Figure 7:
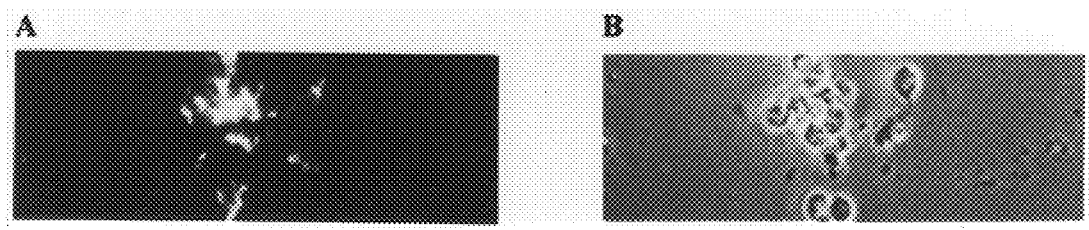
FIGS. 7A and 7B show indirect immunofluorescence assay of intact gametes/zygotes.
Figure 8:
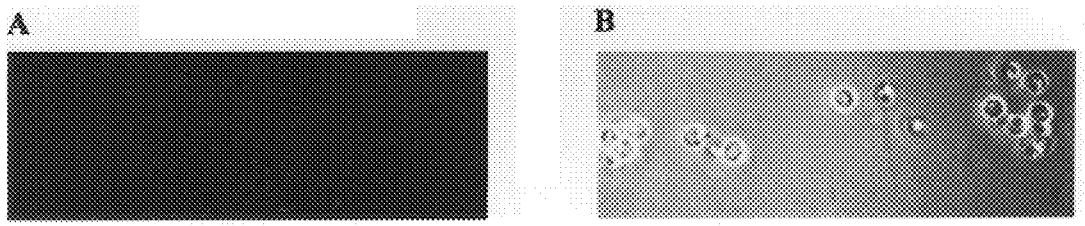
FIGS. 8A and 8B show indirect immunofluorescence assay of intact gametes/zygotes.

Finally, an indirect immunofluorescence assay of intact gametes/zygotes was used to show that rPfs230/MBP-A and B antisera recognized the surface of live gametes/zygotes (FIGS. 6A and 7A). FIGS. 6B and 7B, respectively, are the corresponding bright field image. FIG. 8A shows the results of the same experiment with MBP antisera. FIG. 8B is the corresponding bright field image.

Expression of the Gene in *E. coli*

Pfs230 open reading frame was PCR-amplified using a sense primer with a 5' Sma I site encoding amino acids 439–444 for rPfs230/MBP-A or amino acids 2398–2405 for rPfs230/MBP-B, and an antisense primer with a 3' stop codon followed by a Sal I site encoding amino acid 1127–1135 for rPfs230/MBP-A or nucleotides 9607–9624 in the 3' untranslated region for rPfs230/MBP-B. Gel-purified PCR products were ligated into Stu I/Sma I cut PIH-902 expression vector (gift of Paul Riggs, New England Biolabs). IPTG-induced rPfs230-maltose binding protein fusion was purified from an extract of *E. coli* (DH10B strain, BRL) on amylose resin and use to immunize NIH outbred mice according to the method of Rawlings, et al., *J. Biol. Chem.*, 267: 3976–3982 (1992).

Although the present invention has been described in some detail by way of illustration and example for purposes of clarity and understanding, it will be apparent that certain changes and modifications may be practiced within the scope of the appended claims.

What is claimed is:

1. An isolated Pfs230 polypeptide, wherein the polypeptide is defined as follows:
   (a) having a molecular weight, before processing, of about 363 kDa as measured under reducing conditions; and
   (b) which is expressed by *Plasmodium falciparum* gametocytes.

2. The isolated Pfs230 polypeptide of claim 1, wherein the polypeptide is recombinantly produced.

3. The isolated Pfs230 polypeptide of claim 1, wherein the polypeptide has a sequence as set forth in SEQ ID NO:2.

4. An isolated Pfs230 polypeptide, wherein the polypeptide is defined as follows:
   (a) having a molecular weight of about 310 kDa as measured under reducing conditions; and
   (b) which is expressed on the surface of *Plasmodium falciparum* gametocytes.

5. The isolated Pfs230 polypeptide of claim 4, wherein the polypeptide is recombinantly produced.

6. An isolated Pfs230 polypeptide, wherein the polypeptide is produced by recombinant expression of a nucleic acid having a sequence as set forth in SEQ ID NO:1.

7. A pharmaceutical composition comprising a pharmaceutically acceptable carrier and an isolated Pfs230 polypeptide as defined in claim 1 or 4, wherein the composition is used for immunizing an animal to induce antibodies specifically reactive with the Pfs230 polypeptide.

8. The pharmaceutical composition of claim 7, wherein the polypeptide is recombinantly produced.

9. The pharmaceutical composition of claim 7, wherein the Pfs230 polypeptide has a sequence as set forth in SEQ ID NO:2.

10. The pharmaceutical composition of claim 7, wherein the polypeptide is produced by recombinant expression of a nucleic acid having a sequence as set forth in SEQ ID NO:1.

11. A method for preventing the development of a parasite in an arthropod comprising administering to a patient a pharmaceutical composition comprising a pharmaceutically acceptable carrier and an isolated Pfs230 polypeptide as defined in claim 1 or 4 in an amount sufficient to prevent Pfs230 polypeptide-expressing parasite development in the arthropod.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 9636 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 149..9556

(xi) SEQUENCE DESCRIPTION: SEQ ID NO:1:

```
TATTTTTTTT ATTTTTTTTA TTTTTTTATT TTTTTATTAT TTTTATTTTT TTATTTTTTT      60

TATTTTTTTA TTTTTATATT TTTATATTTT TTTTCTTCTA CCATTCTTTT ATCCTTCTTG     120

ATCGTATATT TTTCTTTTCT TTTAATAA ATG AAG AAA ATT ATA ACG CTG AAG        172
                              Met Lys Lys Ile Ile Thr Leu Lys
                                1               5

AAT CTA TTC CTC ATT ATC CTG GTA TAC ATA TTT AGC GAG AAA AAA GAC       220
Asn Leu Phe Leu Ile Ile Leu Val Tyr Ile Phe Ser Glu Lys Lys Asp
         10              15                  20

CTG CGT TGT AAT GTG ATA AAG GGA AAT AAT ATT AAG GAT GAT GAA GAT       268
Leu Arg Cys Asn Val Ile Lys Gly Asn Asn Ile Lys Asp Asp Glu Asp
 25                  30                  35                  40

AAG AGA TTC CAC TTA TTT TAT TAT TCC CAC AAC CTT TTT AAG ACA CCC       316
Lys Arg Phe His Leu Phe Tyr Tyr Ser His Asn Leu Phe Lys Thr Pro
                 45                  50                  55

GAA ACA AAA GAA AAG AAG AAT AAA AAG GAG TGC TTT TAT AAA AAT GGT       364
Glu Thr Lys Glu Lys Lys Asn Lys Lys Glu Cys Phe Tyr Lys Asn Gly
             60                  65                  70

GGT ATT TAT AAT TTA TCT AAA GAA ATA AGG ATG AGA AAG GAT ACA TCC       412
Gly Ile Tyr Asn Leu Ser Lys Glu Ile Arg Met Arg Lys Asp Thr Ser
         75                  80                  85
```

```
GTA AAA ATA AAA CAA AGA ACA TGT CCC TTT CAT AAA GAA GGA AGT TCA      460
Val Lys Ile Lys Gln Arg Thr Cys Pro Phe His Lys Glu Gly Ser Ser
    90                  95                 100

TTT GAA ATG GGT TCA AAG AAT ATT ACA TGT TTT TAT CCT ATC GTA GGG      508
Phe Glu Met Gly Ser Lys Asn Ile Thr Cys Phe Tyr Pro Ile Val Gly
105                 110                 115                 120

AAG AAG GAA AGG AAA ACA CTG GAC ACA ATT ATT ATA AAA AAG AAT GTA      556
Lys Lys Glu Arg Lys Thr Leu Asp Thr Ile Ile Ile Lys Lys Asn Val
                125                 130                 135

ACA AAT GAT CAT GTT GTT AGT AGT GAT ATG CAT TCC AAT GTA CAA GAA      604
Thr Asn Asp His Val Val Ser Ser Asp Met His Ser Asn Val Gln Glu
            140                 145                 150

AAA AAT ATG ATA TTA ATA AGA AAT ATA GAT AAA GAA AAT AAA AAT GAT      652
Lys Asn Met Ile Leu Ile Arg Asn Ile Asp Lys Glu Asn Lys Asn Asp
        155                 160                 165

ATA CAA AAT GTT GAG GAA AAA ATA CAA AGG GAT ACA TAC GAA AAT AAA      700
Ile Gln Asn Val Glu Glu Lys Ile Gln Arg Asp Thr Tyr Glu Asn Lys
    170                 175                 180

GAT TAT GAA AGT GAT GAT ACA CTT ATA GAA TGG TTT GAT GAT AAT ACA      748
Asp Tyr Glu Ser Asp Asp Thr Leu Ile Glu Trp Phe Asp Asp Asn Thr
185                 190                 195                 200

AAT GAA GAA AAC TTT TTA CTA ACT TTT TTA AAA AGG TGC TTG ATG AAA      796
Asn Glu Glu Asn Phe Leu Leu Thr Phe Leu Lys Arg Cys Leu Met Lys
                205                 210                 215

ATA TTT TCT TCA CCC AAA AGA AAA AAA ACT GTA GTA CAA AAA AAA CAT      844
Ile Phe Ser Ser Pro Lys Arg Lys Lys Thr Val Val Gln Lys Lys His
            220                 225                 230

AAG TCT AAT TTT TTT ATA AAC AGT TCG TTG AAA TAT ATA TAT ATG TAT      892
Lys Ser Asn Phe Phe Ile Asn Ser Ser Leu Lys Tyr Ile Tyr Met Tyr
        235                 240                 245

TTA ACC CCC TCG GAT AGC TTT AAC CTA GTA CGT CGA AAC AGA AAT TTG      940
Leu Thr Pro Ser Asp Ser Phe Asn Leu Val Arg Arg Asn Arg Asn Leu
    250                 255                 260

GAT GAG GAA GAC ATG TCG CCC AGG GAT AAT TTT GTA ATA GAT GAT GAG      988
Asp Glu Glu Asp Met Ser Pro Arg Asp Asn Phe Val Ile Asp Asp Glu
265                 270                 275                 280

GAA GAA GAG GAG GAG GAA GAA GAA GAG GAA GAG GAA GAA GAG GAA GAA     1036
Glu Glu Glu Glu Glu Glu Glu Glu Glu Glu Glu Glu Glu Glu Glu Glu
                285                 290                 295

GAA GAA GAA GAG GAG GAG GAA GAA TAT GAT GAT TAT GTT TAT GAA GAA     1084
Glu Glu Glu Glu Glu Glu Glu Glu Tyr Asp Asp Tyr Val Tyr Glu Glu
            300                 305                 310

AGT GGG GAT GAA ACA GAA GAA CAA TTA CAA GAG GAA CAT CAG GAA GAA     1132
Ser Gly Asp Glu Thr Glu Glu Gln Leu Gln Glu Glu His Gln Glu Glu
        315                 320                 325

GTA GGT GCT GAA TCT TCA GAA GAA AGT TTT AAT GAT GAG GAT GAA GAT     1180
Val Gly Ala Glu Ser Ser Glu Glu Ser Phe Asn Asp Glu Asp Glu Asp
    330                 335                 340

TCT GTA GAA GCA CGG GAT GGA GAT ATG ATA AGA GTT GAC GAA TAT TAT     1228
Ser Val Glu Ala Arg Asp Gly Asp Met Ile Arg Val Asp Glu Tyr Tyr
345                 350                 355                 360

GAA GAC CAA GAT GGT GAT ACT TAT GAT AGT ACA ATA AAA AAT GAA GAT     1276
Glu Asp Gln Asp Gly Asp Thr Tyr Asp Ser Thr Ile Lys Asn Glu Asp
                365                 370                 375

GTA GAT GAA GAG GTA GGT GAA GAG GTA GGT GAA GAG GTA GGT GAA GAG     1324
Val Asp Glu Glu Val Gly Glu Glu Val Gly Glu Glu Val Gly Glu Glu
            380                 385                 390

GTA GGT GAA GAG GTA GGT GAA GAG GTA GGT GAA GAG GTA GGT GAA GAG     1372
Val Gly Glu Glu Val Gly Glu Glu Val Gly Glu Glu Val Gly Glu Glu
        395                 400                 405
```

```
GTA GGT GAA GAG GTA GGT GAA GAA GAA GGT GAA GAG GTA GGT GAA GGG      1420
Val Gly Glu Glu Val Gly Glu Glu Glu Gly Glu Glu Val Gly Glu Gly
        410                 415                 420

GTA GGT GAA GAG GTA GGT GAA GAA GAA GGT GAA GAG GTA GGT GAA GAA      1468
Val Gly Glu Glu Val Gly Glu Glu Glu Gly Glu Glu Val Gly Glu Glu
425                 430                 435                 440

GAA GGT GAA TAT GTA GAT GAA AAA GAA AGG CAA GGT GAA ATA TAT CCA      1516
Glu Gly Glu Tyr Val Asp Glu Lys Glu Arg Gln Gly Glu Ile Tyr Pro
                    445                 450                 455

TTT GGT GAT GAA GAA GAA AAA GAT GAA GGT GGA GAA AGT TTT ACC TAT      1564
Phe Gly Asp Glu Glu Glu Lys Asp Glu Gly Gly Glu Ser Phe Thr Tyr
            460                 465                 470

GAA AAG AGC GAG GTT GAT AAA ACA GAT TTG TTT AAA TTT ATA GAA GGG      1612
Glu Lys Ser Glu Val Asp Lys Thr Asp Leu Phe Lys Phe Ile Glu Gly
        475                 480                 485

GGT GAA GGA GAT GAT GTA TAT AAA GTG GAT GGT TCC AAA GTT TTA TTA      1660
Gly Glu Gly Asp Asp Val Tyr Lys Val Asp Gly Ser Lys Val Leu Leu
    490                 495                 500

GAT GAT GAT ACA ATT AGT AGA GTA TCT AAA AAA CAT ACT GCA CGA GAT      1708
Asp Asp Asp Thr Ile Ser Arg Val Ser Lys Lys His Thr Ala Arg Asp
505                 510                 515                 520

GGT GAA TAT GGT GAA TAT GGT GAA GCT GTC GAA GAT GGA GAA AAT GTT      1756
Gly Glu Tyr Gly Glu Tyr Gly Glu Ala Val Glu Asp Gly Glu Asn Val
                525                 530                 535

ATA AAA ATA ATT AGA AGT GTG TTA CAA AGT GGT GCA TTA CCA AGT GTA      1804
Ile Lys Ile Ile Arg Ser Val Leu Gln Ser Gly Ala Leu Pro Ser Val
            540                 545                 550

GGT GTT GAT GAG TTA GAT AAA ATC GAT TTG TCA TAT GAA ACA ACA GAA      1852
Gly Val Asp Glu Leu Asp Lys Ile Asp Leu Ser Tyr Glu Thr Thr Glu
        555                 560                 565

AGT GGA GAT ACT GCT GTA TCC GAA GAT TCA TAT GAT AAA TAT GCA TCT      1900
Ser Gly Asp Thr Ala Val Ser Glu Asp Ser Tyr Asp Lys Tyr Ala Ser
    570                 575                 580

AAT AAT ACA AAT AAA GAA TAC GTT TGT GAT TTT ACA GAT CAA TTA AAA      1948
Asn Asn Thr Asn Lys Glu Tyr Val Cys Asp Phe Thr Asp Gln Leu Lys
585                 590                 595                 600

CCA ACA GAA AGT GGT CCT AAA GTA AAA AAA TGT GAA GTA AAA GTT AAT      1996
Pro Thr Glu Ser Gly Pro Lys Val Lys Lys Cys Glu Val Lys Val Asn
                605                 610                 615

GAG CCA TTA ATA AAA GTA AAA ATA ATA TGT CCA TTA AAA GGT TCT GTA      2044
Glu Pro Leu Ile Lys Val Lys Ile Ile Cys Pro Leu Lys Gly Ser Val
            620                 625                 630

GAA AAA TTA TAT GAT AAT ATA GAA TAT GTA CCT AAA AAA AGC CCA TAT      2092
Glu Lys Leu Tyr Asp Asn Ile Glu Tyr Val Pro Lys Lys Ser Pro Tyr
        635                 640                 645

GTT GTT TTA ACA AAA GAG GAA ACT AAA CTA AAG GAA AAA CTT CTC TCG      2140
Val Val Leu Thr Lys Glu Glu Thr Lys Leu Lys Glu Lys Leu Leu Ser
    650                 655                 660

AAA CTT ATT TAT GGT TTA TTA ATA TCT CCG ACG GTT AAC GAA AAG GAG      2188
Lys Leu Ile Tyr Gly Leu Leu Ile Ser Pro Thr Val Asn Glu Lys Glu
665                 670                 675                 680

AAT AAT TTT AAA GAA GGT GTT ATT GAA TTT ACT CTT CCC CCT GTG GTA      2236
Asn Asn Phe Lys Glu Gly Val Ile Glu Phe Thr Leu Pro Pro Val Val
                685                 690                 695

CAC AAG GCA ACA GTG TTT TAT TTT ATA TGT GAT AAT TCA AAA ACA GAA      2284
His Lys Ala Thr Val Phe Tyr Phe Ile Cys Asp Asn Ser Lys Thr Glu
            700                 705                 710

GAT GAT AAC AAA AAA GGA AAT AGA GGG ATT GTA GAA GTG TAT GTA GAA      2332
Asp Asp Asn Lys Lys Gly Asn Arg Gly Ile Val Glu Val Tyr Val Glu
```

```
            715                 720                 725
CCA TAT GGT AAT AAA ATT AAT GGA TGT GCT TTC TTG GAT GAA GAT GAA       2380
Pro Tyr Gly Asn Lys Ile Asn Gly Cys Ala Phe Leu Asp Glu Asp Glu
    730                 735                 740

GAA GAA GAA AAA TAT GGT AAT CAA ATT GAA GAA GAT GAA CAT AAT GAG       2428
Glu Glu Glu Lys Tyr Gly Asn Gln Ile Glu Glu Asp Glu His Asn Glu
745                 750                 755                 760

AAG ATA AAA ATG AAA ACA TTC TTT ACC CAG AAT ATA TAT AAA AAA AAT       2476
Lys Ile Lys Met Lys Thr Phe Phe Thr Gln Asn Ile Tyr Lys Lys Asn
                765                 770                 775

AAT ATA TAT CCA TGT TAT ATG AAA TTA TAT AGC GGA GAT ATA GGT GGT       2524
Asn Ile Tyr Pro Cys Tyr Met Lys Leu Tyr Ser Gly Asp Ile Gly Gly
            780                 785                 790

ATT CTA TTT CCT AAG AAT ATA AAA TCA ACA ACG TGT TTT GAA GAG ATG       2572
Ile Leu Phe Pro Lys Asn Ile Lys Ser Thr Thr Cys Phe Glu Glu Met
        795                 800                 805

ATA CCT TAT AAT AAA GAA ATA AAA TGG AAT AAA GAA AAT AAA AGT TTA       2620
Ile Pro Tyr Asn Lys Glu Ile Lys Trp Asn Lys Glu Asn Lys Ser Leu
    810                 815                 820

GGT AAC TTA GTT AAT AAT TCT GTA GTA TAT AAT AAA GAG ATG AAT GCA       2668
Gly Asn Leu Val Asn Asn Ser Val Val Tyr Asn Lys Glu Met Asn Ala
825                 830                 835                 840

AAA TAT TTT AAT GTT CAG TAT GTT CAC ATT CCT ACA AGT TAT AAA GAT       2716
Lys Tyr Phe Asn Val Gln Tyr Val His Ile Pro Thr Ser Tyr Lys Asp
                845                 850                 855

ACA TTA AAT TTA TTT TGT AGT ATT ATA TTA AAA GAA GAG GAA AGT AAT       2764
Thr Leu Asn Leu Phe Cys Ser Ile Ile Leu Lys Glu Glu Glu Ser Asn
            860                 865                 870

TTA ATT TCT ACT TCT TAT TTA GTA TAT GTA AGT ATT AAT GAA GAA TTA       2812
Leu Ile Ser Thr Ser Tyr Leu Val Tyr Val Ser Ile Asn Glu Glu Leu
        875                 880                 885

AAT TTT TCA CTT TTC GAT TTT TAT GAA TCA TTT GTA CCT ATA AAA AAA       2860
Asn Phe Ser Leu Phe Asp Phe Tyr Glu Ser Phe Val Pro Ile Lys Lys
    890                 895                 900

ACC ATA CAA GTA GCT CAA AAG AAT GTA AAT AAT AAA GAA CAT GAT TAT       2908
Thr Ile Gln Val Ala Gln Lys Asn Val Asn Asn Lys Glu His Asp Tyr
905                 910                 915                 920

ACA TGT GAT TTT ACC GAT AAA TTA GAT AAA ACG GTT CCT TCT ACT GCT       2956
Thr Cys Asp Phe Thr Asp Lys Leu Asp Lys Thr Val Pro Ser Thr Ala
                925                 930                 935

AAT GGG AAG AAA TTA TTT ATA TGT AGA AAG CAT TTA AAA GAA TTT GAT       3004
Asn Gly Lys Lys Leu Phe Ile Cys Arg Lys His Leu Lys Glu Phe Asp
            940                 945                 950

ACA TTT ACC TTA AAA TGT AAT GTT AAT AAA ACA CAA TAT CCA AAT ATC       3052
Thr Phe Thr Leu Lys Cys Asn Val Asn Lys Thr Gln Tyr Pro Asn Ile
        955                 960                 965

GAG ATA TTT CCT AAA ACA TTA AAA GAT AAA AAG GAA GTA TTA AAA TTA       3100
Glu Ile Phe Pro Lys Thr Leu Lys Asp Lys Lys Glu Val Leu Lys Leu
    970                 975                 980

GAT CTT GAT ATA CAA TAT CAA ATG TTT AGT AAA TTT TTT AAA TTC AAT       3148
Asp Leu Asp Ile Gln Tyr Gln Met Phe Ser Lys Phe Phe Lys Phe Asn
985                 990                 995                 1000

ACA CAG AAT GCA AAG TAT TTA AAT TTA TAT CCA TAT TAT TTA ATT TTT       3196
Thr Gln Asn Ala Lys Tyr Leu Asn Leu Tyr Pro Tyr Tyr Leu Ile Phe
                1005                1010                1015

CCA TTT AAT CAT ATA GGA AAA AAA GAA TTA AAA AAT AAT CCT ACA TAT       3244
Pro Phe Asn His Ile Gly Lys Lys Glu Leu Lys Asn Asn Pro Thr Tyr
            1020                1025                1030

AAA AAT CAT AAA GAT GTG AAA TAT TTT GAG CAA TCA TCT GTA TTA TCT       3292
```

```
                                                         -continued

Lys Asn His Lys Asp Val Lys Tyr Phe Glu Gln Ser Ser Val Leu Ser
        1035                1040                1045

CCC TTA TCT TCC GCA GAC AGT TTA GGG AAA TTA TTA AAT TTT TTA GAT          3340
Pro Leu Ser Ser Ala Asp Ser Leu Gly Lys Leu Leu Asn Phe Leu Asp
    1050                1055                1060

ACT CAA GAG ACG GTA TGT CTT ACG GAA AAG ATA AGA TAT TTA AAT TTA          3388
Thr Gln Glu Thr Val Cys Leu Thr Glu Lys Ile Arg Tyr Leu Asn Leu
1065                1070                1075                1080

AGT ATC AAT GAG TTA GGA TCT GAT AAT AAT ACA TTT TCT GTA ACA TTT          3436
Ser Ile Asn Glu Leu Gly Ser Asp Asn Asn Thr Phe Ser Val Thr Phe
                    1085                1090                1095

CAG GTT CCA CCA TAT ATA GAT ATT AAG GAA CCT TTT TAT TTT ATG TTT          3484
Gln Val Pro Pro Tyr Ile Asp Ile Lys Glu Pro Phe Tyr Phe Met Phe
            1100                1105                1110

GGT TGT AAT AAT AAT AAA GGT GAA GGG AAT ATC GGA ATT GTT GAA TTA          3532
Gly Cys Asn Asn Asn Lys Gly Glu Gly Asn Ile Gly Ile Val Glu Leu
        1115                1120                1125

TTA ATA TCT AAG CAA GAA GAA AAG ATT AAA GGA TGT AAT TTC CAT GAA          3580
Leu Ile Ser Lys Gln Glu Glu Lys Ile Lys Gly Cys Asn Phe His Glu
    1130                1135                1140

TCT AAA TTA GAT TAT TTC AAT GAA AAC ATT TCT AGT GAT ACA CAT GAA          3628
Ser Lys Leu Asp Tyr Phe Asn Glu Asn Ile Ser Ser Asp Thr His Glu
1145                1150                1155                1160

TGT ACA TTG CAT GCA TAT GAA AAT GAT ATA ATT GGA TTT AAT TGT TTA          3676
Cys Thr Leu His Ala Tyr Glu Asn Asp Ile Ile Gly Phe Asn Cys Leu
                    1165                1170                1175

GAA ACT ACT CAT CCT AAT GAG GTT GAG GTT GAA GTT GAA GAT GCT GAA          3724
Glu Thr Thr His Pro Asn Glu Val Glu Val Glu Val Glu Asp Ala Glu
            1180                1185                1190

ATA TAT CTT CAA CCT GAG AAT TGT TTT AAT AAT GTA TAT AAA GGA TTG          3772
Ile Tyr Leu Gln Pro Glu Asn Cys Phe Asn Asn Val Tyr Lys Gly Leu
        1195                1200                1205

AAT TCT GTT GAT ATT ACT ACT ATA TTA AAA AAT GCA CAA ACA TAT AAT          3820
Asn Ser Val Asp Ile Thr Thr Ile Leu Lys Asn Ala Gln Thr Tyr Asn
    1210                1215                1220

ATA AAT AAT AAG AAA ACA CCT ACC TTT TTA AAA ATT CCA CCA TAT AAT          3868
Ile Asn Asn Lys Lys Thr Pro Thr Phe Leu Lys Ile Pro Pro Tyr Asn
1225                1230                1235                1240

TTA TTA GAA GAT GTC GAA ATT AGT TGC CAA TGT ACT ATT AAA CAA GTT          3916
Leu Leu Glu Asp Val Glu Ile Ser Cys Gln Cys Thr Ile Lys Gln Val
                    1245                1250                1255

GTT AAA AAA ATA AAA GTT ATT ATA ACC AAA AAT GAT ACA GTA TTA TTA          3964
Val Lys Lys Ile Lys Val Ile Ile Thr Lys Asn Asp Thr Val Leu Leu
            1260                1265                1270

AAA AGA GAA GTG CAA TCT GAG TCT ACA TTA GAT GAT AAA ATA TAT AAA          4012
Lys Arg Glu Val Gln Ser Glu Ser Thr Leu Asp Asp Lys Ile Tyr Lys
        1275                1280                1285

TGT GAA CAT GAA AAT TTT ATT AAT CCA AGA GTA AAT AAA ACA TTT GAT          4060
Cys Glu His Glu Asn Phe Ile Asn Pro Arg Val Asn Lys Thr Phe Asp
    1290                1295                1300

GAA AAT GTA GAA TAT ACA TGT AAT ATA AAA ATA GAG AAT TTC TTT AAT          4108
Glu Asn Val Glu Tyr Thr Cys Asn Ile Lys Ile Glu Asn Phe Phe Asn
1305                1310                1315                1320

TAT ATT CAA ATA TTT TGT CCA GCC AAA GAT CTT GGT ATT TAT AAA AAT          4156
Tyr Ile Gln Ile Phe Cys Pro Ala Lys Asp Leu Gly Ile Tyr Lys Asn
                    1325                1330                1335

ATA CAA ATG TAT TAT GAT ATT GTA AAA CCA ACA AGA GTA CCA CAA TTT          4204
Ile Gln Met Tyr Tyr Asp Ile Val Lys Pro Thr Arg Val Pro Gln Phe
            1340                1345                1350
```

-continued

```
AAA AAA TTT AAT AAT GAA GAA TTA CAT AAA TTA ATT CCT AAT TCA GAA    4252
Lys Lys Phe Asn Asn Glu Glu Leu His Lys Leu Ile Pro Asn Ser Glu
        1355                1360                1365

ATG TTA CAT AAA ACA AAA GAA ATG TTA ATT TTA TAT AAT GAA GAA AAA    4300
Met Leu His Lys Thr Lys Glu Met Leu Ile Leu Tyr Asn Glu Glu Lys
        1370                1375                1380

GTG GAT CTA TTA CAT TTT TAT GTA TTC TTA CCA ATA TAT ATA AAA GAC    4348
Val Asp Leu Leu His Phe Tyr Val Phe Leu Pro Ile Tyr Ile Lys Asp
1385                1390                1395                1400

ATA TAT GAA TTC AAT ATA GTA TGT GAT AAT TCA AAA ACA ATG TGG AAA    4396
Ile Tyr Glu Phe Asn Ile Val Cys Asp Asn Ser Lys Thr Met Trp Lys
                1405                1410                1415

AAT CAA TTA GGA GGA AAA GTT ATA TAT CAT ATT ACT GTT TCA AAA AGA    4444
Asn Gln Leu Gly Gly Lys Val Ile Tyr His Ile Thr Val Ser Lys Arg
        1420                1425                1430

GAG CAG AAA GTA AAA GGT TGT TCA TTT GAT AAT GAA CAT GCA CAT ATG    4492
Glu Gln Lys Val Lys Gly Cys Ser Phe Asp Asn Glu His Ala His Met
        1435                1440                1445

TTT AGT TAT AAT AAA ACT AAT GTA AAA AAT TGT ATT ATA GAT GCT AAA    4540
Phe Ser Tyr Asn Lys Thr Asn Val Lys Asn Cys Ile Ile Asp Ala Lys
        1450                1455                1460

CCT AAA GAT TTG ATA GGT TTC GTT TGT CCC TCT GGT ACC TTA AAA TTA    4588
Pro Lys Asp Leu Ile Gly Phe Val Cys Pro Ser Gly Thr Leu Lys Leu
1465                1470                1475                1480

ACA AAT TGT TTT AAA GAT GCA ATA GTA CAT ACA AAT TTA ACA AAT ATT    4636
Thr Asn Cys Phe Lys Asp Ala Ile Val His Thr Asn Leu Thr Asn Ile
                1485                1490                1495

AAT GGT ATA CTT TAT TTA AAA AAT AAT TTG GCT AAC TTT ACA TAT AAA    4684
Asn Gly Ile Leu Tyr Leu Lys Asn Asn Leu Ala Asn Phe Thr Tyr Lys
        1500                1505                1510

CAT CAA TTT AAT TAT ATG GAA ATA CCA GCT TTA ATG GAT AAT GAT ATA    4732
His Gln Phe Asn Tyr Met Glu Ile Pro Ala Leu Met Asp Asn Asp Ile
        1515                1520                1525

TCA TTT AAA TGT ATA TGT GTT GAT TTA AAA AAA AAA AAA TAT AAT GTC    4780
Ser Phe Lys Cys Ile Cys Val Asp Leu Lys Lys Lys Lys Tyr Asn Val
        1530                1535                1540

AAA TCA CCA TTA GGA CCT AAA GTT TTA CGT GCT CTT TAT AAA AAA TTA    4828
Lys Ser Pro Leu Gly Pro Lys Val Leu Arg Ala Leu Tyr Lys Lys Leu
1545                1550                1555                1560

AAT ATA AAA TTT GAT AAT TAT GTT ACT GGC ACT GAT CAA AAT AAA TAT    4876
Asn Ile Lys Phe Asp Asn Tyr Val Thr Gly Thr Asp Gln Asn Lys Tyr
                1565                1570                1575

CTT ATG ACA TAT ATG GAT TTA CAT TTA TCT CAT AAA CGT AAT TAT TTA    4924
Leu Met Thr Tyr Met Asp Leu His Leu Ser His Lys Arg Asn Tyr Leu
        1580                1585                1590

AAG GAA TTA TTT CAT GAT TTA GGT AAA AAA AAA CCA GCA GAT ACA GAT    4972
Lys Glu Leu Phe His Asp Leu Gly Lys Lys Lys Pro Ala Asp Thr Asp
        1595                1600                1605

GCT AAC CCT GAA TCT ATT ATC GAA TCT TTA AGT ATT AAT GAA TCT AAT    5020
Ala Asn Pro Glu Ser Ile Ile Glu Ser Leu Ser Ile Asn Glu Ser Asn
        1610                1615                1620

GAA TCT GGA CCT TTT CCA ACC GGG GAT GTA GAT GCA GAA CAT TTA ATA    5068
Glu Ser Gly Pro Phe Pro Thr Gly Asp Val Asp Ala Glu His Leu Ile
1625                1630                1635                1640

TTA GAA GGA TAT GAT ACA TGG GAA AGT TTA TAT GAT GAA CAA TTA GAA    5116
Leu Glu Gly Tyr Asp Thr Trp Glu Ser Leu Tyr Asp Glu Gln Leu Glu
                1645                1650                1655

GAA GTT ATA TAT AAT GAT ATT GAA TCT TTA GAA TTA AAA GAT ATT GAA    5164
Glu Val Ile Tyr Asn Asp Ile Glu Ser Leu Glu Leu Lys Asp Ile Glu
        1660                1665                1670
```

-continued

```
CAA TAT GTT TTA CAA GTT AAT TTA AAA GCT CCA AAA TTA ATG ATG TCT       5212
Gln Tyr Val Leu Gln Val Asn Leu Lys Ala Pro Lys Leu Met Met Ser
            1675                1680                1685

GCT CAA ATT CAT AAT AAT AGA CAT GTA TGT GAT TTC TCA AAA AAT AAT       5260
Ala Gln Ile His Asn Asn Arg His Val Cys Asp Phe Ser Lys Asn Asn
        1690                1695                1700

TTA ATT GTA CCA GAA TCA TTA AAA AAA AAA GAG CTT GGT GGT AAT           5308
Leu Ile Val Pro Glu Ser Leu Lys Lys Lys Glu Leu Gly Gly Asn
1705                1710                1715                1720

CCA GTA AAT ATT CAT TGT TAT GCA TTA TTA AAA CCT TTA GAT ACA TTA       5356
Pro Val Asn Ile His Cys Tyr Ala Leu Leu Lys Pro Leu Asp Thr Leu
            1725                1730                1735

TAT GTA AAA TGT CCT ACA TCA AAA GAT AAT TAT GAA GCT GCT AAA GTA       5404
Tyr Val Lys Cys Pro Thr Ser Lys Asp Asn Tyr Glu Ala Ala Lys Val
        1740                1745                1750

AAC ATA TCT GAA AAC GAC AAT GAA TAT GAG TTA CAA GTT ATA TCA TTA       5452
Asn Ile Ser Glu Asn Asp Asn Glu Tyr Glu Leu Gln Val Ile Ser Leu
            1755                1760                1765

ATC GAA AAA AGA TTT CAT AAT TTT GAG ACG TTA GAA TCG AAG AAA CCT       5500
Ile Glu Lys Arg Phe His Asn Phe Glu Thr Leu Glu Ser Lys Lys Pro
        1770                1775                1780

GGA AAT GGA GAT GTA GTA GTA CAT AAT GGT GTT GTA GAT ACT GGA CCT       5548
Gly Asn Gly Asp Val Val Val His Asn Gly Val Val Asp Thr Gly Pro
1785                1790                1795                1800

GTA TTA GAT AAC AGT ACA TTT GAA AAA TAT TTT AAA AAT ATA AAA ATA       5596
Val Leu Asp Asn Ser Thr Phe Glu Lys Tyr Phe Lys Asn Ile Lys Ile
            1805                1810                1815

AAA CCA GAT AAA TTT TTT GAG AAA GTT ATA AAT GAA TAT GAT GAT ACT       5644
Lys Pro Asp Lys Phe Phe Glu Lys Val Ile Asn Glu Tyr Asp Asp Thr
        1820                1825                1830

GAA GAA GAA AAA GAT TTA GAA AGT ATA TTA CCT GGG GCT ATT GTT AGT       5692
Glu Glu Glu Lys Asp Leu Glu Ser Ile Leu Pro Gly Ala Ile Val Ser
            1835                1840                1845

CCT ATG AAA GTT TTA AAA AAA AAG GAT CCT TTT ACA TCA TAT GCT GCT       5740
Pro Met Lys Val Leu Lys Lys Lys Asp Pro Phe Thr Ser Tyr Ala Ala
        1850                1855                1860

TTT GTT GTT CCA CCA ATT GTT CCC AAA GAT TTA CAT TTT AAA GTA GAA       5788
Phe Val Val Pro Pro Ile Val Pro Lys Asp Leu His Phe Lys Val Glu
1865                1870                1875                1880

TGT AAT AAT ACA GAA TAT AAA GAT GAA AAT CAA TAT ATA AGT GGA TAT       5836
Cys Asn Asn Thr Glu Tyr Lys Asp Glu Asn Gln Tyr Ile Ser Gly Tyr
            1885                1890                1895

AAT GGT ATA ATA CAT ATT GAT ATA TCA AAT AGT AAT AGG AAA ATT AAT       5884
Asn Gly Ile Ile His Ile Asp Ile Ser Asn Ser Asn Arg Lys Ile Asn
        1900                1905                1910

GGA TGT GAT TTC TCT ACG AAC AAT AGT TCT ATT TTA ACA TCC AGT GTA       5932
Gly Cys Asp Phe Ser Thr Asn Asn Ser Ser Ile Leu Thr Ser Ser Val
            1915                1920                1925

AAA TTA GTA AAT GGA GAA ACT AAA AAT TGT GAA ATA AAT ATA AAT AAT       5980
Lys Leu Val Asn Gly Glu Thr Lys Asn Cys Glu Ile Asn Ile Asn Asn
        1930                1935                1940

AAT GAA GTA TTT GGT ATC ATA TGT GAT AAT GAA ACA AAT TTA GAT CCA       6028
Asn Glu Val Phe Gly Ile Ile Cys Asp Asn Glu Thr Asn Leu Asp Pro
1945                1950                1955                1960

GAA AAA TGT TTT CAT GAA ATA TAT AGT AAA GAT AAT AAA ACT GTA AAA       6076
Glu Lys Cys Phe His Glu Ile Tyr Ser Lys Asp Asn Lys Thr Val Lys
            1965                1970                1975

AAA TTT CGT GAA GTT ATA CCT AAT ATA GAT ATA TTC TCA TTA CAT AAT       6124
Lys Phe Arg Glu Val Ile Pro Asn Ile Asp Ile Phe Ser Leu His Asn
```

-continued

```
              1980                1985                1990

TCT AAT AAG AAA AAA GTT GCA TAT GCT AAA GTA CCT TTA GAT TAT ATT    6172
Ser Asn Lys Lys Lys Val Ala Tyr Ala Lys Val Pro Leu Asp Tyr Ile
        1995                2000                2005

AAT AAA TTA TTA TTT TCT TGT TCA TGT AAA ACA TCA CAT ACT AAT ACA    6220
Asn Lys Leu Leu Phe Ser Cys Ser Cys Lys Thr Ser His Thr Asn Thr
        2010                2015                2020

ATA GGT ACC ATG AAA GTT ACT CTA AAT AAA GAT GAA AAA GAA GAA GAA    6268
Ile Gly Thr Met Lys Val Thr Leu Asn Lys Asp Glu Lys Glu Glu Glu
2025                2030                2035                2040

GAT TTT AAA ACA GCT CAA GGT ATT AAA CAT AAT AAT GTA CAT TTA TGT    6316
Asp Phe Lys Thr Ala Gln Gly Ile Lys His Asn Asn Val His Leu Cys
            2045                2050                2055

AAT TTC TTT GAT AAT CCT GAA TTA ACA TTT GAT AAT AAT AAA ATA GTT    6364
Asn Phe Phe Asp Asn Pro Glu Leu Thr Phe Asp Asn Asn Lys Ile Val
            2060                2065                2070

TTA TGT AAA ATC GAT GCA GAA CTG TTC TCA GAA GTA ATT ATA CAA TTA    6412
Leu Cys Lys Ile Asp Ala Glu Leu Phe Ser Glu Val Ile Ile Gln Leu
        2075                2080                2085

CCA ATA TTT GGA ACA AAG AAT GTA GAA GAA GGA GTA CAA AAT GAA GAA    6460
Pro Ile Phe Gly Thr Lys Asn Val Glu Glu Gly Val Gln Asn Glu Glu
        2090                2095                2100

TAT AAA AAA TTT TCA TTA AAA CCA TCA TTA GTT TTT GAT GAT AAC AAT    6508
Tyr Lys Lys Phe Ser Leu Lys Pro Ser Leu Val Phe Asp Asp Asn Asn
2105                2110                2115                2120

AAT GAT ATT AAA GTT ATA GGA AAA GAA AAA AAT GAA GTA TCT ATT AGT    6556
Asn Asp Ile Lys Val Ile Gly Lys Glu Lys Asn Glu Val Ser Ile Ser
            2125                2130                2135

TTA GCT TTG AAA GGG GTT TAT GGA AAT CGA ATT TTT ACT TTT GAT AAA    6604
Leu Ala Leu Lys Gly Val Tyr Gly Asn Arg Ile Phe Thr Phe Asp Lys
            2140                2145                2150

AAT GGA AAA AAA GGA GAA GGA ATT AGT TTT TTT ATA CCT CCA ATA AAA    6652
Asn Gly Lys Lys Gly Glu Gly Ile Ser Phe Phe Ile Pro Pro Ile Lys
        2155                2160                2165

CAA GAT ACA GAT TTA AAA TTT ATA ATT AAT GAA ACA ATA GAT AAT TCA    6700
Gln Asp Thr Asp Leu Lys Phe Ile Ile Asn Glu Thr Ile Asp Asn Ser
        2170                2175                2180

AAT ATT AAA CAA AGA GGA TTA ATA TAT ATT TTT GTT AGG AAA AAT GTA    6748
Asn Ile Lys Gln Arg Gly Leu Ile Tyr Ile Phe Val Arg Lys Asn Val
2185                2190                2195                2200

TCA GAA AAT TCA TTT AAA TTA TGT GAT TTC ACA ACA GGT TCG ACT TCA    6796
Ser Glu Asn Ser Phe Lys Leu Cys Asp Phe Thr Thr Gly Ser Thr Ser
            2205                2210                2215

TTA ATG GAA TTA AAT AGT CAA GTA AAA GAA AAA AAG TGC ACT GTT AAA    6844
Leu Met Glu Leu Asn Ser Gln Val Lys Glu Lys Lys Cys Thr Val Lys
            2220                2225                2230

ATT AAA AAA GGA GAT ATT TTT GGA TTG AAA TGT CCT AAA GGT TTT GCT    6892
Ile Lys Lys Gly Asp Ile Phe Gly Leu Lys Cys Pro Lys Gly Phe Ala
            2235                2240                2245

ATA TTT CCA CAA GCA TGT TTT AGT AAT GTT TTA TTA GAA TAT TAT AAA    6940
Ile Phe Pro Gln Ala Cys Phe Ser Asn Val Leu Leu Glu Tyr Tyr Lys
            2250                2255                2260

AGT GAT TAT GAA GAT AGT GAA CAT ATT AAT TAT TAT ATT CAT AAA GAT    6988
Ser Asp Tyr Glu Asp Ser Glu His Ile Asn Tyr Tyr Ile His Lys Asp
2265                2270                2275                2280

AAA AAA TAT AAT TTA AAA CCT AAA GAT GTT ATT GAA TTA ATG GAT GAA    7036
Lys Lys Tyr Asn Leu Lys Pro Lys Asp Val Ile Glu Leu Met Asp Glu
            2285                2290                2295

AAT TTT AGA GAA TTA CAA AAT ATA CAA CAA TAT ACA GGA ATA TCA AAT    7084
```

```
Asn Phe Arg Glu Leu Gln Asn Ile Gln Gln Tyr Thr Gly Ile Ser Asn
            2300                2305                2310

ATT ACA GAT GTG TTA CAT TTC AAA AAT TTT AAT TTA GGT AAT CTA CCA        7132
Ile Thr Asp Val Leu His Phe Lys Asn Phe Asn Leu Gly Asn Leu Pro
            2315                2320                2325

TTA AAT TTT AAA AAT CAT TAT TCT ACA GCA TAT GCT AAA GTA CCA GAT        7180
Leu Asn Phe Lys Asn His Tyr Ser Thr Ala Tyr Ala Lys Val Pro Asp
            2330                2335                2340

ACC TTT AAT TCT ATT ATT AAC TTC TCA TGT AAT TGT TAT AAT CCA GAA        7228
Thr Phe Asn Ser Ile Ile Asn Phe Ser Cys Asn Cys Tyr Asn Pro Glu
2345                2350                2355                2360

AAA CAT GTA TAT GGT ACT ATG CAA GTT GAG TCT GAT AAT CGA AAT TTT        7276
Lys His Val Tyr Gly Thr Met Gln Val Glu Ser Asp Asn Arg Asn Phe
            2365                2370                2375

GAT AAT ATT AAA AAA AAT GAA AAT GTT ATA AAA AAT TTC CTT TTA CCT        7324
Asp Asn Ile Lys Lys Asn Glu Asn Val Ile Lys Asn Phe Leu Leu Pro
            2380                2385                2390

AAT ATA GAA AAA TAT GCA CTA CTA TTA GAT GAT GAA GAA AGA CAA AAA        7372
Asn Ile Glu Lys Tyr Ala Leu Leu Leu Asp Asp Glu Glu Arg Gln Lys
            2395                2400                2405

AAA ATA AAA CAA CAA CAA GAA GAA GAA CAA CAA GAA CAA ATA TTA AAA        7420
Lys Ile Lys Gln Gln Gln Glu Glu Glu Gln Gln Glu Gln Ile Leu Lys
            2410                2415                2420

GAT CAA GAT GAT AGA TTA AGC AGA CAT GAT GAT TAT AAT AAA AAT CAT        7468
Asp Gln Asp Asp Arg Leu Ser Arg His Asp Asp Tyr Asn Lys Asn His
2425                2430                2435                2440

ACA TAT ATA CTA TAT GAT TCA AAT GAA CAT ATA TGT GAT TAT GAA AAA        7516
Thr Tyr Ile Leu Tyr Asp Ser Asn Glu His Ile Cys Asp Tyr Glu Lys
            2445                2450                2455

AAT GAA TCA CTC ATA TCA ACA TTA CCT AAT GAT ACA AAA AAA ATA CAA        7564
Asn Glu Ser Leu Ile Ser Thr Leu Pro Asn Asp Thr Lys Lys Ile Gln
            2460                2465                2470

AAA AGT ATC TGT AAA ATT AAT GCA AAA GCA TTA GAT GTT GTT ACA ATT        7612
Lys Ser Ile Cys Lys Ile Asn Ala Lys Ala Leu Asp Val Val Thr Ile
            2475                2480                2485

AAA TGT CCT CAT ACA AAA AAT TTT ACG CCT AAA GAT TAT TTT CCT AAT        7660
Lys Cys Pro His Thr Lys Asn Phe Thr Pro Lys Asp Tyr Phe Pro Asn
            2490                2495                2500

TCT TCA TTA ATA ACT AAT GAT AAA AAA ATT GTG ATT ACT TTT GAT AAG        7708
Ser Ser Leu Ile Thr Asn Asp Lys Lys Ile Val Ile Thr Phe Asp Lys
2505                2510                2515                2520

AAA AAT TTT GTT ACT TAT ATA GAT CCT ACA AAA AAA ACA TTT TCT TTG        7756
Lys Asn Phe Val Thr Tyr Ile Asp Pro Thr Lys Lys Thr Phe Ser Leu
            2525                2530                2535

AAA GAT ATA TAT ATA CAA AGT TTT TAT GGT GTT TCT CTT GAT CAT CTT        7804
Lys Asp Ile Tyr Ile Gln Ser Phe Tyr Gly Val Ser Leu Asp His Leu
            2540                2545                2550

AAT CAA ATA AAA AAA ATA CAT GAA GAA TGG GAT GAT GTA CAT TTA TTT        7852
Asn Gln Ile Lys Lys Ile His Glu Glu Trp Asp Asp Val His Leu Phe
            2555                2560                2565

TAT CCT CCT CAT AAT GTA TTA CAT AAT GTT GTA CTT AAT AAT CAT ATA        7900
Tyr Pro Pro His Asn Val Leu His Asn Val Val Leu Asn Asn His Ile
            2570                2575                2580

GTC AAC TTA TCA TCT GCA TTA GAA GGA GTC TTA TTT ATG AAA TCA AAA        7948
Val Asn Leu Ser Ser Ala Leu Glu Gly Val Leu Phe Met Lys Ser Lys
2585                2590                2595                2600

GTT ACT GGA GAT GAA ACA GCT ACA AAA AAA AAC ACT ACA CTA CCA ACT        7996
Val Thr Gly Asp Glu Thr Ala Thr Lys Lys Asn Thr Thr Leu Pro Thr
            2605                2610                2615
```

```
GAT GGT GTA TCA AGT ATT TTA ATT CCA CCA TAT GTA AAG GAA GAT ATA      8044
Asp Gly Val Ser Ser Ile Leu Ile Pro Pro Tyr Val Lys Glu Asp Ile
            2620              2625              2630

ACA TTT CAT CTT TTT TGT GGG AAA TCT ACA ACA AAA AAA CCA AAC AAA      8092
Thr Phe His Leu Phe Cys Gly Lys Ser Thr Thr Lys Lys Pro Asn Lys
        2635              2640              2645

AAG AAC ACA TCT CTT GCA CTT ATT CAT ATA CAT ATA TCA TCA AAC AGA      8140
Lys Asn Thr Ser Leu Ala Leu Ile His Ile His Ile Ser Ser Asn Arg
        2650              2655              2660

AAT ATT ATT CAT GGA TGT GAT TTC TTA TAT TTA GAA AAT CAA ACA AAT      8188
Asn Ile Ile His Gly Cys Asp Phe Leu Tyr Leu Glu Asn Gln Thr Asn
2665              2670              2675              2680

GAT GCT ATT AGT AAT AAT AAT AAT AAT TCA TAT TCT ATA TTT ACA CAT      8236
Asp Ala Ile Ser Asn Asn Asn Asn Asn Ser Tyr Ser Ile Phe Thr His
            2685              2690              2695

AAT AAA AAT ACA GAG AAT AAT CTA ATA TGT GAT ATA TCT TTA ATT CCA      8284
Asn Lys Asn Thr Glu Asn Asn Leu Ile Cys Asp Ile Ser Leu Ile Pro
        2700              2705              2710

AAA ACT GTT ATA GGA ATT AAA TGT CCT AAT AAA AAA TTA AAT CCA CAA      8332
Lys Thr Val Ile Gly Ile Lys Cys Pro Asn Lys Lys Leu Asn Pro Gln
        2715              2720              2725

ACA TGT TTT GAT GAA GTG TAT TAT GTT AAA CAA GAA GAT GTA CCT TCG      8380
Thr Cys Phe Asp Glu Val Tyr Tyr Val Lys Gln Glu Asp Val Pro Ser
        2730              2735              2740

AAA ACT ATA ACA GCT GAT AAA TAT AAT ACA TTT AGT AAA GAC AAA ATA      8428
Lys Thr Ile Thr Ala Asp Lys Tyr Asn Thr Phe Ser Lys Asp Lys Ile
2745              2750              2755              2760

GGA AAT ATA TTA AAA AAT GCA ATC TCT ATT AAT AAT CCA GAT GAA AAG      8476
Gly Asn Ile Leu Lys Asn Ala Ile Ser Ile Asn Asn Pro Asp Glu Lys
            2765              2770              2775

GAT AAT ACA TAT ACT TAT TTA ATA TTA CCA GAA AAA TTT GAA GAA GAA      8524
Asp Asn Thr Tyr Thr Tyr Leu Ile Leu Pro Glu Lys Phe Glu Glu Glu
        2780              2785              2790

TTA ATC GAT ACC AAA AAA GTT TTA GCT TGT ACA TGT GAT AAT AAA TAT      8572
Leu Ile Asp Thr Lys Lys Val Leu Ala Cys Thr Cys Asp Asn Lys Tyr
        2795              2800              2805

ATA ATA CAT ATG AAA ATA GAA AAA AGT ACA ATG GAT AAA ATA AAA ATA      8620
Ile Ile His Met Lys Ile Glu Lys Ser Thr Met Asp Lys Ile Lys Ile
        2810              2815              2820

GAT GAA AAA AAA ACA ATT GGT AAA GAT ATA TGT AAA TAT GAT GTT ACT      8668
Asp Glu Lys Lys Thr Ile Gly Lys Asp Ile Cys Lys Tyr Asp Val Thr
2825              2830              2835              2840

ACT AAA GTT GCT ACT TGT GAA ATT ATT GAT ACA ATT GAT TCG TCT GTA      8716
Thr Lys Val Ala Thr Cys Glu Ile Ile Asp Thr Ile Asp Ser Ser Val
            2845              2850              2855

TTA AAA GAA CAT CAT ACA GTA CAT TAT TCT ATT ACA TTA TCA AGA TGG      8764
Leu Lys Glu His His Thr Val His Tyr Ser Ile Thr Leu Ser Arg Trp
        2860              2865              2870

GAT AAA CTT ATT ATT AAA TAT CCA ACA AAT GAG AAA ACA CAT TTC GAA      8812
Asp Lys Leu Ile Ile Lys Tyr Pro Thr Asn Glu Lys Thr His Phe Glu
        2875              2880              2885

AAT TTT TTT GTT AAT CCT TTT AAT TTA AAA GAT AAA GTT TTA TAT AAT      8860
Asn Phe Phe Val Asn Pro Phe Asn Leu Lys Asp Lys Val Leu Tyr Asn
        2890              2895              2900

TAT AAT AAA CCA ATA AAT ATA GAA CAT ATC TTA CCA GGA GCC ATT ACA      8908
Tyr Asn Lys Pro Ile Asn Ile Glu His Ile Leu Pro Gly Ala Ile Thr
2905              2910              2915              2920

ACA GAT ATA TAT GAT ACC AGA ACA AAA ATT AAA CAA TAT ATA TTA AGA      8956
Thr Asp Ile Tyr Asp Thr Arg Thr Lys Ile Lys Gln Tyr Ile Leu Arg
            2925              2930              2935
```

-continued

```
ATT CCA CCA TAT GTA CAT AAA GAT ATA CAT TTC TCA TTA GAA TTT AAC       9004
Ile Pro Pro Tyr Val His Lys Asp Ile His Phe Ser Leu Glu Phe Asn
        2940            2945            2950

AAT AGC CTA AGT TTA ACA AAA CAA AAT CAA AAT ATT ATT TAT GGA AAT       9052
Asn Ser Leu Ser Leu Thr Lys Gln Asn Gln Asn Ile Ile Tyr Gly Asn
        2955            2960            2965

GTA GCC AAA ATT TTT ATT CAT ATA AAT CAA GGA TAT AAA GAA ATT CAT       9100
Val Ala Lys Ile Phe Ile His Ile Asn Gln Gly Tyr Lys Glu Ile His
        2970            2975            2980

GGA TGT GAT TTC ACA GGA AAA TAT TCC CAT TTA TTT ACA TAT TCA AAA       9148
Gly Cys Asp Phe Thr Gly Lys Tyr Ser His Leu Phe Thr Tyr Ser Lys
2985            2990            2995            3000

AAA CCT TTA CCA AAT GAT GAT GAT ATA TGT AAT GTA ACT ATA GGT AAT       9196
Lys Pro Leu Pro Asn Asp Asp Asp Ile Cys Asn Val Thr Ile Gly Asn
        3005            3010            3015

AAT ACA TTC TCA GGT TTT GCA TGC TTA AGC CAT TTT GAA TTA AAA CCA       9244
Asn Thr Phe Ser Gly Phe Ala Cys Leu Ser His Phe Glu Leu Lys Pro
        3020            3025            3030

AAT AAC TGC TTC TCA TCT GTT TAT GAT TAT AAT GAA GCC AAT AAA GTT       9292
Asn Asn Cys Phe Ser Ser Val Tyr Asp Tyr Asn Glu Ala Asn Lys Val
        3035            3040            3045

AAA AAA TTA TTC GAT CTA TCC ACA AAA GTA GAA TTA GAC CAT ATC AAA       9340
Lys Lys Leu Phe Asp Leu Ser Thr Lys Val Glu Leu Asp His Ile Lys
        3050            3055            3060

CAA AAT ACT TCA GGA TAT ACA CTA TCA TAT ATT ATT TTT AAT AAA GAA       9388
Gln Asn Thr Ser Gly Tyr Thr Leu Ser Tyr Ile Ile Phe Asn Lys Glu
3065            3070            3075            3080

TCC ACA AAA CTT AAA TTC TCA TGT ACA TGC TCA TCC AAC TAT TCA AAT       9436
Ser Thr Lys Leu Lys Phe Ser Cys Thr Cys Ser Ser Asn Tyr Ser Asn
        3085            3090            3095

TAT ACT ATA CGA ATC ACA TTT GAT CCT AAT TAT ATA ATC CCA GAA CCT       9484
Tyr Thr Ile Arg Ile Thr Phe Asp Pro Asn Tyr Ile Ile Pro Glu Pro
        3100            3105            3110

CAA TCA AGA GCC ATC ATT AAA TAT GTA GAT CTG CAA GAT AAA AAT TTT       9532
Gln Ser Arg Ala Ile Ile Lys Tyr Val Asp Leu Gln Asp Lys Asn Phe
        3115            3120            3125

GCA AAA TAC TTG AGA AAG CTT TAAATCGTAA ATAATTAATC AAACATATAT          9583
Ala Lys Tyr Leu Arg Lys Leu
        3130            3135

ATAATCAAAA GGATAATATA TTAGAACACA CATATATATG TAAAAAAAAA AAA            9636

(2) INFORMATION FOR SEQ ID NO:2:

(i) SEQUENCE CHARACTERISTICS:
        (A) LENGTH: 3135 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Lys Ile Ile Thr Leu Lys Asn Leu Phe Leu Ile Ile Leu Val
1               5                   10                  15

Tyr Ile Phe Ser Glu Lys Lys Asp Leu Arg Cys Asn Val Ile Lys Gly
                20                  25                  30

Asn Asn Ile Lys Asp Asp Glu Asp Lys Arg Phe His Leu Phe Tyr Tyr
            35                  40                  45

Ser His Asn Leu Phe Lys Thr Pro Glu Thr Lys Glu Lys Lys Asn Lys
        50                  55                  60
```

-continued

```
Lys Glu Cys Phe Tyr Lys Asn Gly Gly Ile Tyr Asn Leu Ser Lys Glu
 65                  70                  75                  80

Ile Arg Met Arg Lys Asp Thr Ser Val Lys Ile Lys Gln Arg Thr Cys
                 85                  90                  95

Pro Phe His Lys Glu Gly Ser Ser Phe Glu Met Gly Ser Lys Asn Ile
                100                 105                 110

Thr Cys Phe Tyr Pro Ile Val Gly Lys Lys Glu Arg Lys Thr Leu Asp
            115                 120                 125

Thr Ile Ile Ile Lys Lys Asn Val Thr Asn Asp His Val Val Ser Ser
        130                 135                 140

Asp Met His Ser Asn Val Gln Glu Lys Asn Met Ile Leu Ile Arg Asn
145                 150                 155                 160

Ile Asp Lys Glu Asn Lys Asn Asp Ile Gln Asn Val Glu Glu Lys Ile
                165                 170                 175

Gln Arg Asp Thr Tyr Glu Asn Lys Asp Tyr Glu Ser Asp Asp Thr Leu
            180                 185                 190

Ile Glu Trp Phe Asp Asp Asn Thr Asn Glu Glu Asn Phe Leu Leu Thr
        195                 200                 205

Phe Leu Lys Arg Cys Leu Met Lys Ile Phe Ser Ser Pro Lys Arg Lys
    210                 215                 220

Lys Thr Val Val Gln Lys Lys His Lys Ser Asn Phe Phe Ile Asn Ser
225                 230                 235                 240

Ser Leu Lys Tyr Ile Tyr Met Tyr Leu Thr Pro Ser Asp Ser Phe Asn
                245                 250                 255

Leu Val Arg Arg Asn Arg Asn Leu Asp Glu Glu Asp Met Ser Pro Arg
            260                 265                 270

Asp Asn Phe Val Ile Asp Asp Glu Glu Glu Glu Glu Glu Glu Glu Glu
        275                 280                 285

Glu Glu Glu Glu Glu Glu Glu Glu Glu Glu Glu Glu Glu Glu Glu Glu
    290                 295                 300

Tyr Asp Asp Tyr Val Tyr Glu Glu Ser Gly Asp Glu Thr Glu Glu Gln
305                 310                 315                 320

Leu Gln Glu Glu His Gln Glu Glu Val Gly Ala Glu Ser Ser Glu Glu
                325                 330                 335

Ser Phe Asn Asp Glu Asp Glu Asp Ser Val Glu Ala Arg Asp Gly Asp
            340                 345                 350

Met Ile Arg Val Asp Glu Tyr Tyr Glu Asp Gln Asp Gly Asp Thr Tyr
        355                 360                 365

Asp Ser Thr Ile Lys Asn Glu Asp Val Asp Glu Glu Val Gly Glu Glu
    370                 375                 380

Val Gly Glu Glu Val Gly Glu Glu Val Gly Glu Glu Val Gly Glu Glu
385                 390                 395                 400

Val Gly Glu Glu Val Gly Glu Glu Val Gly Glu Glu Val Gly Glu Glu
                405                 410                 415

Glu Gly Glu Glu Val Gly Glu Glu Val Gly Glu Glu Val Gly Glu Glu
            420                 425                 430

Glu Gly Glu Glu Val Gly Glu Glu Gly Glu Tyr Val Asp Glu Lys
        435                 440                 445

Glu Arg Gln Gly Glu Ile Tyr Pro Phe Gly Asp Glu Glu Lys Asp
    450                 455                 460

Glu Gly Gly Glu Ser Phe Thr Tyr Glu Lys Ser Glu Val Asp Lys Thr
465                 470                 475                 480

Asp Leu Phe Lys Phe Ile Glu Gly Gly Glu Gly Asp Asp Val Tyr Lys
```

-continued

```
                485                 490                 495
Val Asp Gly Ser Lys Val Leu Leu Asp Asp Thr Ile Ser Arg Val
                500                 505                 510

Ser Lys Lys His Thr Ala Arg Asp Gly Glu Tyr Gly Glu Tyr Gly Glu
                515                 520                 525

Ala Val Glu Asp Gly Glu Asn Val Ile Lys Ile Ile Arg Ser Val Leu
        530                 535                 540

Gln Ser Gly Ala Leu Pro Ser Val Gly Val Asp Glu Leu Asp Lys Ile
545                 550                 555                 560

Asp Leu Ser Tyr Glu Thr Thr Glu Ser Gly Asp Thr Ala Val Ser Glu
                    565                 570                 575

Asp Ser Tyr Asp Lys Tyr Ala Ser Asn Asn Thr Asn Lys Glu Tyr Val
            580                 585                 590

Cys Asp Phe Thr Asp Gln Leu Lys Pro Thr Glu Ser Gly Pro Lys Val
                595                 600                 605

Lys Lys Cys Glu Val Lys Val Asn Glu Pro Leu Ile Lys Val Lys Ile
        610                 615                 620

Ile Cys Pro Leu Lys Gly Ser Val Glu Lys Leu Tyr Asp Asn Ile Glu
625                 630                 635                 640

Tyr Val Pro Lys Lys Ser Pro Tyr Val Val Leu Thr Lys Glu Glu Thr
                    645                 650                 655

Lys Leu Lys Glu Lys Leu Leu Ser Lys Leu Ile Tyr Gly Leu Leu Ile
            660                 665                 670

Ser Pro Thr Val Asn Glu Lys Glu Asn Asn Phe Lys Glu Gly Val Ile
                675                 680                 685

Glu Phe Thr Leu Pro Pro Val Val His Lys Ala Thr Val Phe Tyr Phe
        690                 695                 700

Ile Cys Asp Asn Ser Lys Thr Glu Asp Asp Asn Lys Lys Gly Asn Arg
705                 710                 715                 720

Gly Ile Val Glu Val Tyr Val Glu Pro Tyr Gly Asn Lys Ile Asn Gly
                    725                 730                 735

Cys Ala Phe Leu Asp Glu Asp Glu Glu Glu Lys Tyr Gly Asn Gln
            740                 745                 750

Ile Glu Glu Asp Glu His Asn Glu Lys Ile Lys Met Lys Thr Phe Phe
        755                 760                 765

Thr Gln Asn Ile Tyr Lys Lys Asn Asn Ile Tyr Pro Cys Tyr Met Lys
770                 775                 780

Leu Tyr Ser Gly Asp Ile Gly Gly Ile Leu Phe Pro Lys Asn Ile Lys
785                 790                 795                 800

Ser Thr Thr Cys Phe Glu Glu Met Ile Pro Tyr Asn Lys Glu Ile Lys
                    805                 810                 815

Trp Asn Lys Glu Asn Lys Ser Leu Gly Asn Leu Val Asn Asn Ser Val
            820                 825                 830

Val Tyr Asn Lys Glu Met Asn Ala Lys Tyr Phe Asn Val Gln Tyr Val
        835                 840                 845

His Ile Pro Thr Ser Tyr Lys Asp Thr Leu Asn Leu Phe Cys Ser Ile
        850                 855                 860

Ile Leu Lys Glu Glu Ser Asn Leu Ile Ser Thr Ser Tyr Leu Val
865                 870                 875                 880

Tyr Val Ser Ile Asn Glu Glu Leu Asn Phe Ser Leu Phe Asp Phe Tyr
                    885                 890                 895

Glu Ser Phe Val Pro Ile Lys Lys Thr Ile Gln Val Ala Gln Lys Asn
            900                 905                 910
```

-continued

Val Asn Asn Lys Glu His Asp Tyr Thr Cys Asp Phe Thr Asp Lys Leu
            915                 920                 925

Asp Lys Thr Val Pro Ser Thr Ala Asn Gly Lys Lys Leu Phe Ile Cys
    930                 935                 940

Arg Lys His Leu Lys Glu Phe Asp Thr Phe Thr Leu Lys Cys Asn Val
945                 950                 955                 960

Asn Lys Thr Gln Tyr Pro Asn Ile Glu Ile Phe Pro Lys Thr Leu Lys
            965                 970                 975

Asp Lys Lys Glu Val Leu Lys Leu Asp Leu Asp Ile Gln Tyr Gln Met
                980                 985                 990

Phe Ser Lys Phe Phe Lys Phe Asn Thr Gln Asn Ala Lys Tyr Leu Asn
            995                 1000                1005

Leu Tyr Pro Tyr Tyr Leu Ile Phe Pro Phe Asn His Ile Gly Lys Lys
            1010                1015                1020

Glu Leu Lys Asn Asn Pro Thr Tyr Lys Asn His Lys Asp Val Lys Tyr
1025                1030                1035                1040

Phe Glu Gln Ser Ser Val Leu Ser Pro Leu Ser Ser Ala Asp Ser Leu
                1045                1050                1055

Gly Lys Leu Leu Asn Phe Leu Asp Thr Gln Glu Thr Val Cys Leu Thr
            1060                1065                1070

Glu Lys Ile Arg Tyr Leu Asn Leu Ser Ile Asn Glu Leu Gly Ser Asp
            1075                1080                1085

Asn Asn Thr Phe Ser Val Thr Phe Gln Val Pro Pro Tyr Ile Asp Ile
            1090                1095                1100

Lys Glu Pro Phe Tyr Phe Met Phe Gly Cys Asn Asn Asn Lys Gly Glu
1105                1110                1115                1120

Gly Asn Ile Gly Ile Val Glu Leu Leu Ile Ser Lys Gln Glu Glu Lys
            1125                1130                1135

Ile Lys Gly Cys Asn Phe His Glu Ser Lys Leu Asp Tyr Phe Asn Glu
            1140                1145                1150

Asn Ile Ser Ser Asp Thr His Glu Cys Thr Leu His Ala Tyr Glu Asn
            1155                1160                1165

Asp Ile Ile Gly Phe Asn Cys Leu Glu Thr Thr His Pro Asn Glu Val
            1170                1175                1180

Glu Val Glu Val Glu Asp Ala Glu Ile Tyr Leu Gln Pro Glu Asn Cys
1185                1190                1195                1200

Phe Asn Asn Val Tyr Lys Gly Leu Asn Ser Val Asp Ile Thr Thr Ile
                1205                1210                1215

Leu Lys Asn Ala Gln Thr Tyr Asn Ile Asn Asn Lys Lys Thr Pro Thr
                1220                1225                1230

Phe Leu Lys Ile Pro Pro Tyr Asn Leu Leu Glu Asp Val Glu Ile Ser
            1235                1240                1245

Cys Gln Cys Thr Ile Lys Gln Val Val Lys Ile Lys Val Ile Ile
            1250                1255                1260

Thr Lys Asn Asp Thr Val Leu Leu Lys Arg Glu Val Gln Ser Glu Ser
1265                1270                1275                1280

Thr Leu Asp Asp Lys Ile Tyr Lys Cys Glu His Glu Asn Phe Ile Asn
                1285                1290                1295

Pro Arg Val Asn Lys Thr Phe Asp Glu Asn Val Glu Tyr Thr Cys Asn
            1300                1305                1310

Ile Lys Ile Glu Asn Phe Phe Asn Tyr Ile Gln Ile Phe Cys Pro Ala
            1315                1320                1325

-continued

```
Lys Asp Leu Gly Ile Tyr Lys Asn Ile Gln Met Tyr Tyr Asp Ile Val
        1330            1335            1340

Lys Pro Thr Arg Val Pro Gln Phe Lys Phe Asn Asn Glu Glu Leu
1345            1350            1355            1360

His Lys Leu Ile Pro Asn Ser Glu Met Leu His Lys Thr Lys Glu Met
                1365            1370            1375

Leu Ile Leu Tyr Asn Glu Glu Lys Val Asp Leu Leu His Phe Tyr Val
        1380            1385            1390

Phe Leu Pro Ile Tyr Ile Lys Asp Ile Tyr Glu Phe Asn Ile Val Cys
            1395            1400            1405

Asp Asn Ser Lys Thr Met Trp Lys Asn Gln Leu Gly Gly Lys Val Ile
        1410            1415            1420

Tyr His Ile Thr Val Ser Lys Arg Glu Gln Lys Val Lys Gly Cys Ser
1425            1430            1435            1440

Phe Asp Asn Glu His Ala His Met Phe Ser Tyr Asn Lys Thr Asn Val
                1445            1450            1455

Lys Asn Cys Ile Ile Asp Ala Lys Pro Lys Asp Leu Ile Gly Phe Val
                1460            1465            1470

Cys Pro Ser Gly Thr Leu Lys Leu Thr Asn Cys Phe Lys Asp Ala Ile
            1475            1480            1485

Val His Thr Asn Leu Thr Asn Ile Asn Gly Ile Leu Tyr Leu Lys Asn
        1490            1495            1500

Asn Leu Ala Asn Phe Thr Tyr Lys His Gln Phe Asn Tyr Met Glu Ile
1505            1510            1515            1520

Pro Ala Leu Met Asp Asn Asp Ile Ser Phe Lys Cys Ile Cys Val Asp
                1525            1530            1535

Leu Lys Lys Lys Lys Tyr Asn Val Lys Ser Pro Leu Gly Pro Lys Val
                1540            1545            1550

Leu Arg Ala Leu Tyr Lys Lys Leu Asn Ile Lys Phe Asp Asn Tyr Val
            1555            1560            1565

Thr Gly Thr Asp Gln Asn Lys Tyr Leu Met Thr Tyr Met Asp Leu His
    1570            1575            1580

Leu Ser His Lys Arg Asn Tyr Leu Lys Glu Leu Phe His Asp Leu Gly
1585            1590            1595            1600

Lys Lys Lys Pro Ala Asp Thr Asp Ala Asn Pro Glu Ser Ile Ile Glu
            1605            1610            1615

Ser Leu Ser Ile Asn Glu Ser Asn Glu Ser Gly Pro Phe Pro Thr Gly
            1620            1625            1630

Asp Val Asp Ala Glu His Leu Ile Leu Glu Gly Tyr Asp Thr Trp Glu
        1635            1640            1645

Ser Leu Tyr Asp Glu Gln Leu Glu Glu Val Ile Tyr Asn Asp Ile Glu
    1650            1655            1660

Ser Leu Glu Leu Lys Asp Ile Glu Gln Tyr Val Leu Gln Val Asn Leu
1665            1670            1675            1680

Lys Ala Pro Lys Leu Met Met Ser Ala Gln Ile His Asn Asn Arg His
            1685            1690            1695

Val Cys Asp Phe Ser Lys Asn Asn Leu Ile Val Pro Glu Ser Leu Lys
            1700            1705            1710

Lys Lys Glu Glu Leu Gly Gly Asn Pro Val Asn Ile His Cys Tyr Ala
            1715            1720            1725

Leu Leu Lys Pro Leu Asp Thr Leu Tyr Val Lys Cys Pro Thr Ser Lys
        1730            1735            1740

Asp Asn Tyr Glu Ala Ala Lys Val Asn Ile Ser Glu Asn Asp Asn Glu
```

-continued

```
1745                1750                1755                1760

Tyr Glu Leu Gln Val Ile Ser Leu Ile Glu Lys Arg Phe His Asn Phe
                1765                1770                1775

Glu Thr Leu Glu Ser Lys Lys Pro Gly Asn Gly Asp Val Val His
            1780                1785                1790

Asn Gly Val Val Asp Thr Gly Pro Val Leu Asp Asn Ser Thr Phe Glu
        1795                1800                1805

Lys Tyr Phe Lys Asn Ile Lys Ile Lys Pro Asp Lys Phe Glu Lys
        1810                1815                1820

Val Ile Asn Glu Tyr Asp Asp Thr Glu Glu Lys Asp Leu Glu Ser
1825                1830                1835                1840

Ile Leu Pro Gly Ala Ile Val Ser Pro Met Lys Val Leu Lys Lys
                1845                1850                1855

Asp Pro Phe Thr Ser Tyr Ala Ala Phe Val Pro Pro Ile Val Pro
                1860                1865                1870

Lys Asp Leu His Phe Lys Val Glu Cys Asn Asn Thr Glu Tyr Lys Asp
        1875                1880                1885

Glu Asn Gln Tyr Ile Ser Gly Tyr Asn Gly Ile Ile His Ile Asp Ile
        1890                1895                1900

Ser Asn Ser Asn Arg Lys Ile Asn Gly Cys Asp Phe Ser Thr Asn Asn
1905                1910                1915                1920

Ser Ser Ile Leu Thr Ser Ser Val Lys Leu Val Asn Gly Glu Thr Lys
            1925                1930                1935

Asn Cys Glu Ile Asn Ile Asn Asn Glu Val Phe Gly Ile Ile Cys
            1940                1945                1950

Asp Asn Glu Thr Asn Leu Asp Pro Glu Lys Cys Phe His Glu Ile Tyr
        1955                1960                1965

Ser Lys Asp Asn Lys Thr Val Lys Lys Phe Arg Glu Val Ile Pro Asn
    1970                1975                1980

Ile Asp Ile Phe Ser Leu His Asn Ser Asn Lys Lys Val Ala Tyr
1985                1990                1995                2000

Ala Lys Val Pro Leu Asp Tyr Ile Asn Lys Leu Leu Phe Ser Cys Ser
                2005                2010                2015

Cys Lys Thr Ser His Thr Asn Thr Ile Gly Thr Met Lys Val Thr Leu
                2020                2025                2030

Asn Lys Asp Glu Lys Glu Glu Asp Phe Lys Thr Ala Gln Gly Ile
            2035                2040                2045

Lys His Asn Asn Val His Leu Cys Asn Phe Phe Asp Asn Pro Glu Leu
        2050                2055                2060

Thr Phe Asp Asn Asn Lys Ile Val Leu Cys Lys Ile Asp Ala Glu Leu
2065                2070                2075                2080

Phe Ser Glu Val Ile Ile Gln Leu Pro Ile Phe Gly Thr Lys Asn Val
                2085                2090                2095

Glu Glu Gly Val Gln Asn Glu Glu Tyr Lys Lys Phe Ser Leu Lys Pro
            2100                2105                2110

Ser Leu Val Phe Asp Asp Asn Asn Asp Ile Lys Val Ile Gly Lys
        2115                2120                2125

Glu Lys Asn Glu Val Ser Ile Ser Leu Ala Leu Lys Gly Val Tyr Gly
        2130                2135                2140

Asn Arg Ile Phe Thr Phe Asp Lys Asn Gly Lys Lys Gly Glu Gly Ile
2145                2150                2155                2160

Ser Phe Phe Ile Pro Pro Ile Lys Gln Asp Thr Asp Leu Lys Phe Ile
                2165                2170                2175
```

-continued

```
Ile Asn Glu Thr Ile Asp Asn Ser Asn Ile Lys Gln Arg Gly Leu Ile
            2180                2185                2190
Tyr Ile Phe Val Arg Lys Asn Val Ser Glu Asn Ser Phe Lys Leu Cys
        2195                2200                2205
Asp Phe Thr Thr Gly Ser Thr Ser Leu Met Glu Leu Asn Ser Gln Val
        2210                2215                2220
Lys Glu Lys Lys Cys Thr Val Lys Ile Lys Lys Gly Asp Ile Phe Gly
2225            2230                2235                2240
Leu Lys Cys Pro Lys Gly Phe Ala Ile Phe Pro Gln Ala Cys Phe Ser
                2245                2250                2255
Asn Val Leu Leu Glu Tyr Tyr Lys Ser Asp Tyr Glu Asp Ser Glu His
            2260                2265                2270
Ile Asn Tyr Tyr Ile His Lys Asp Lys Lys Tyr Asn Leu Lys Pro Lys
        2275                2280                2285
Asp Val Ile Glu Leu Met Asp Glu Asn Phe Arg Glu Leu Gln Asn Ile
        2290                2295                2300
Gln Gln Tyr Thr Gly Ile Ser Asn Ile Thr Asp Val Leu His Phe Lys
2305            2310                2315                2320
Asn Phe Asn Leu Gly Asn Leu Pro Leu Asn Phe Lys Asn His Tyr Ser
                2325                2330                2335
Thr Ala Tyr Ala Lys Val Pro Asp Thr Phe Asn Ser Ile Ile Asn Phe
            2340                2345                2350
Ser Cys Asn Cys Tyr Asn Pro Glu Lys His Val Tyr Gly Thr Met Gln
        2355                2360                2365
Val Glu Ser Asp Asn Arg Asn Phe Asp Asn Ile Lys Lys Asn Glu Asn
        2370                2375                2380
Val Ile Lys Asn Phe Leu Leu Pro Asn Ile Glu Lys Tyr Ala Leu Leu
2385            2390                2395                2400
Leu Asp Asp Glu Glu Arg Gln Lys Lys Ile Lys Gln Gln Gln Glu Glu
                2405                2410                2415
Glu Gln Gln Glu Gln Ile Leu Lys Asp Gln Asp Asp Arg Leu Ser Arg
            2420                2425                2430
His Asp Asp Tyr Asn Lys Asn His Thr Tyr Ile Leu Tyr Asp Ser Asn
        2435                2440                2445
Glu His Ile Cys Asp Tyr Glu Lys Asn Glu Ser Leu Ile Ser Thr Leu
        2450                2455                2460
Pro Asn Asp Thr Lys Lys Ile Gln Lys Ser Ile Cys Lys Ile Asn Ala
2465            2470                2475                2480
Lys Ala Leu Asp Val Val Thr Ile Lys Cys Pro His Thr Lys Asn Phe
                2485                2490                2495
Thr Pro Lys Asp Tyr Phe Pro Asn Ser Ser Leu Ile Thr Asn Asp Lys
            2500                2505                2510
Lys Ile Val Ile Thr Phe Asp Lys Lys Asn Phe Val Thr Tyr Ile Asp
        2515                2520                2525
Pro Thr Lys Lys Thr Phe Ser Leu Lys Asp Ile Tyr Ile Gln Ser Phe
        2530                2535                2540
Tyr Gly Val Ser Leu Asp His Leu Asn Gln Ile Lys Lys Ile His Glu
2545            2550                2555                2560
Glu Trp Asp Asp Val His Leu Phe Tyr Pro Pro His Asn Val Leu His
                2565                2570                2575
Asn Val Val Leu Asn Asn His Ile Val Asn Leu Ser Ser Ala Leu Glu
            2580                2585                2590
```

-continued

```
Gly Val Leu Phe Met Lys Ser Lys Val Thr Gly Asp Glu Thr Ala Thr
            2595                2600                2605
Lys Lys Asn Thr Thr Leu Pro Thr Asp Gly Val Ser Ser Ile Leu Ile
2610                2615                2620
Pro Pro Tyr Val Lys Glu Asp Ile Thr Phe His Leu Phe Cys Gly Lys
2625                2630                2635                2640
Ser Thr Thr Lys Lys Pro Asn Lys Lys Asn Thr Ser Leu Ala Leu Ile
            2645                2650                2655
His Ile His Ile Ser Ser Asn Arg Asn Ile Ile His Gly Cys Asp Phe
            2660                2665                2670
Leu Tyr Leu Glu Asn Gln Thr Asn Asp Ala Ile Ser Asn Asn Asn Asn
            2675                2680                2685
Asn Ser Tyr Ser Ile Phe Thr His Asn Lys Asn Thr Glu Asn Asn Leu
            2690                2695                2700
Ile Cys Asp Ile Ser Leu Ile Pro Lys Thr Val Ile Gly Ile Lys Cys
2705                2710                2715                2720
Pro Asn Lys Lys Leu Asn Pro Gln Thr Cys Phe Asp Glu Val Tyr Tyr
            2725                2730                2735
Val Lys Gln Glu Asp Val Pro Ser Lys Thr Ile Thr Ala Asp Lys Tyr
            2740                2745                2750
Asn Thr Phe Ser Lys Asp Lys Ile Gly Asn Ile Leu Lys Asn Ala Ile
            2755                2760                2765
Ser Ile Asn Asn Pro Asp Glu Lys Asp Asn Thr Tyr Thr Tyr Leu Ile
2770                2775                2780
Leu Pro Glu Lys Phe Glu Glu Leu Ile Asp Thr Lys Lys Val Leu
2785                2790                2795                2800
Ala Cys Thr Cys Asp Asn Lys Tyr Ile Ile His Met Lys Ile Glu Lys
            2805                2810                2815
Ser Thr Met Asp Lys Ile Lys Ile Asp Glu Lys Lys Thr Ile Gly Lys
            2820                2825                2830
Asp Ile Cys Lys Tyr Asp Val Thr Thr Lys Val Ala Thr Cys Glu Ile
            2835                2840                2845
Ile Asp Thr Ile Asp Ser Ser Val Leu Lys Glu His His Thr Val His
2850                2855                2860
Tyr Ser Ile Thr Leu Ser Arg Trp Asp Lys Leu Ile Ile Lys Tyr Pro
2865                2870                2875                2880
Thr Asn Glu Lys Thr His Phe Glu Asn Phe Val Asn Pro Phe Asn
            2885                2890                2895
Leu Lys Asp Lys Val Leu Tyr Asn Tyr Asn Lys Pro Ile Asn Ile Glu
            2900                2905                2910
His Ile Leu Pro Gly Ala Ile Thr Thr Asp Ile Tyr Asp Thr Arg Thr
            2915                2920                2925
Lys Ile Lys Gln Tyr Ile Leu Arg Ile Pro Pro Tyr Val His Lys Asp
            2930                2935                2940
Ile His Phe Ser Leu Glu Phe Asn Asn Ser Leu Ser Leu Thr Lys Gln
2945                2950                2955                2960
Asn Gln Asn Ile Ile Tyr Gly Asn Val Ala Lys Ile Phe Ile His Ile
            2965                2970                2975
Asn Gln Gly Tyr Lys Glu Ile His Gly Cys Asp Phe Thr Gly Lys Tyr
            2980                2985                2990
Ser His Leu Phe Thr Tyr Ser Lys Lys Pro Leu Pro Asn Asp Asp Asp
            2995                3000                3005
Ile Cys Asn Val Thr Ile Gly Asn Asn Thr Phe Ser Gly Phe Ala Cys
```

-continued

```
              3010                3015                3020
Leu Ser His Phe Glu Leu Lys Pro Asn Asn Cys Phe Ser Ser Val Tyr
3025                3030                3035                3040
Asp Tyr Asn Glu Ala Asn Lys Val Lys Lys Leu Phe Asp Leu Ser Thr
                3045                3050                3055
Lys Val Glu Leu Asp His Ile Lys Gln Asn Thr Ser Gly Tyr Thr Leu
                3060                3065                3070
Ser Tyr Ile Ile Phe Asn Lys Glu Ser Thr Lys Leu Lys Phe Ser Cys
            3075                3080                3085
Thr Cys Ser Ser Asn Tyr Ser Asn Tyr Thr Ile Arg Ile Thr Phe Asp
        3090                3095                3100
Pro Asn Tyr Ile Ile Pro Glu Pro Gln Ser Arg Ala Ile Ile Lys Tyr
3105                3110                3115                3120
Val Asp Leu Gln Asp Lys Asn Phe Ala Lys Tyr Leu Arg Lys Leu
                3125                3130                3135

(2) INFORMATION FOR SEQ ID NO:3:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:3:

Glu Glu Val Gly
1

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /note= "Xaa = Glu or Gly"

(ix) FEATURE:
        (A) NAME/KEY: Modified-site
        (B) LOCATION: 7
        (D) OTHER INFORMATION: /product= "OTHER"
            /note= "Xaa = Glu or Val"

(xi) SEQUENCE DESCRIPTION: SEQ ID NO:4:

Glu Glu Val Gly Glu Xaa Xaa Gly
1               5
```